(12) United States Patent
Iwase et al.

(10) Patent No.: US 10,048,141 B2
(45) Date of Patent: Aug. 14, 2018

(54) PRESSURE SENSING ELEMENT AND PRESSURE SENSOR

(71) Applicant: NIPPON MEKTRON, LTD., Tokyo (JP)

(72) Inventors: Masayuki Iwase, Tokyo (JP); Keizo Toyama, Tokyo (JP); Kazuyuki Ozaki, Tokyo (JP); Hirokazu Ohdate, Tokyo (JP); Taisuke Kimura, Tokyo (JP); Ryoichi Toyoshima, Tokyo (JP)

(73) Assignee: NIPPON MEKTRON, LTD., Tokyo (JP)

( * ) Notice: Subject to any disclaimer, the term of this patent is extended or adjusted under 35 U.S.C. 154(b) by 161 days.

(21) Appl. No.: 14/904,782

(22) PCT Filed: Dec. 24, 2014

(86) PCT No.: PCT/JP2014/084084
§ 371 (c)(1),
(2) Date: Jan. 13, 2016

(87) PCT Pub. No.: WO2016/103350
PCT Pub. Date: Jun. 30, 2016

(65) Prior Publication Data
US 2016/0327441 A1 Nov. 10, 2016

(51) Int. Cl.
*G01L 1/04* (2006.01)
*G01L 1/22* (2006.01)
(Continued)

(52) U.S. Cl.
CPC .......... *G01L 1/2287* (2013.01); *A61B 5/1036* (2013.01); *A61B 5/1117* (2013.01);
(Continued)

(58) Field of Classification Search
CPC ....... G01L 1/2287; G01L 1/2231; G01L 1/14; G01L 1/04; G01L 1/205; G01L 1/2206;
(Continued)

(56) References Cited

U.S. PATENT DOCUMENTS 5,997,996 A    12/1999  Tamura
6,388,556 B1 *  5/2002  Imai .................... G01L 1/20
                                                338/114

(Continued)

FOREIGN PATENT DOCUMENTS

CN    101532890 A    9/2009
CN    103180390 A    6/2013
(Continued)

OTHER PUBLICATIONS

International Search Report dated Apr. 7, 2015, issued in counterpart International Application No. PCT/JP2014/084084 (2 pages).
(Continued)

*Primary Examiner* — Manish S Shah
*Assistant Examiner* — Nigel Plumb
(74) *Attorney, Agent, or Firm* — Westerman, Hattori, Daniels & Adrian, LLP

(57) ABSTRACT

Provided is a pressure sensing element configured to be flexible, and capable of demonstrating a stable electrical reliability over a long period; and, a pressure sensor having such pressure sensing element. A pressure sensing element (100) has an electro-conductive pressure sensing film (14), a sensor electrode (12) provided at a position faced to the pressure sensing film (14), and an insulating layer (13) which creates a predetermined distance "A" between the pressure sensing film (14) and the sensor electrode (12) so as to keep them apart from each other, the pressure sensing film (14) being a resin film containing carbon particles (140); and, a pressure sensor (200) has the pressure sensing
(Continued)

element (100), and a detection unit (210) which is electrically connected with the pressure sensing element (100) so as to detect contact resistance between the pressure sensing film (14) and the sensor electrode (12).

14 Claims, 10 Drawing Sheets

(51) Int. Cl.
    *A61B 5/103*    (2006.01)
    *A61B 5/11*     (2006.01)
    *G01L 1/20*     (2006.01)

(52) U.S. Cl.
    CPC ............ G01L 1/205 (2013.01); G01L 1/2206 (2013.01); *A61B 2562/0247* (2013.01); *A61B 2562/125* (2013.01)

(58) Field of Classification Search
    CPC .......... G01L 3/10; G01L 3/24; A61B 5/1036; A61B 5/1117; A61B 2562/125; A61B 2562/0247; B60R 2021/01516
    USPC ...... 73/862.627, 862.625, 862.621, 862.325, 73/862.381, 862
    See application file for complete search history.

(56) References Cited

U.S. PATENT DOCUMENTS

| | | | |
|---|---|---|---|
| 8,161,826 B1* | 4/2012 | Taylor | G01L 1/18 73/862.041 |
| 2004/0000195 A1* | 1/2004 | Yanai | A61B 5/113 73/717 |
| 2009/0226689 A1 | 9/2009 | Watanabe et al. | |
| 2013/0270487 A1* | 10/2013 | Oku | C08G 73/1021 252/511 |
| 2014/0090488 A1* | 4/2014 | Taylor | G01L 1/18 73/862.625 |
| 2014/0109698 A1* | 4/2014 | Lussey | H01C 10/10 73/862.627 |
| 2014/0150571 A1* | 6/2014 | Kuniyoshi | G01L 1/205 73/862.625 |

FOREIGN PATENT DOCUMENTS

| | | | | |
|---|---|---|---|---|
| JP | 64-13677 U | 1/1989 | | |
| JP | 2001-159569 A | 6/2001 | | |
| JP | 2002-158103 A | 5/2002 | | |
| JP | 2003-344195 A | 12/2003 | | |
| JP | 2004-28883 A | 1/2004 | | |
| JP | 2005-351653 A | 12/2005 | | |
| JP | 2006-184098 A | 7/2006 | | |
| JP | 2006184098 | * | 7/2006 | ............... G01L 5/00 |
| JP | 2011-144270 A | 7/2011 | | |
| JP | 2012-236886 A | 12/2012 | | |
| JP | 2012-247372 A | 12/2012 | | |

OTHER PUBLICATIONS

Office Action dated Mar. 5, 2018, issued in Chinese Patent Application No. 201480037448.9.

Extended European Search Report dated Jun. 29, 2018, issued in Application No. 14890459.2 (PCT/JP2014/084084).

* cited by examiner

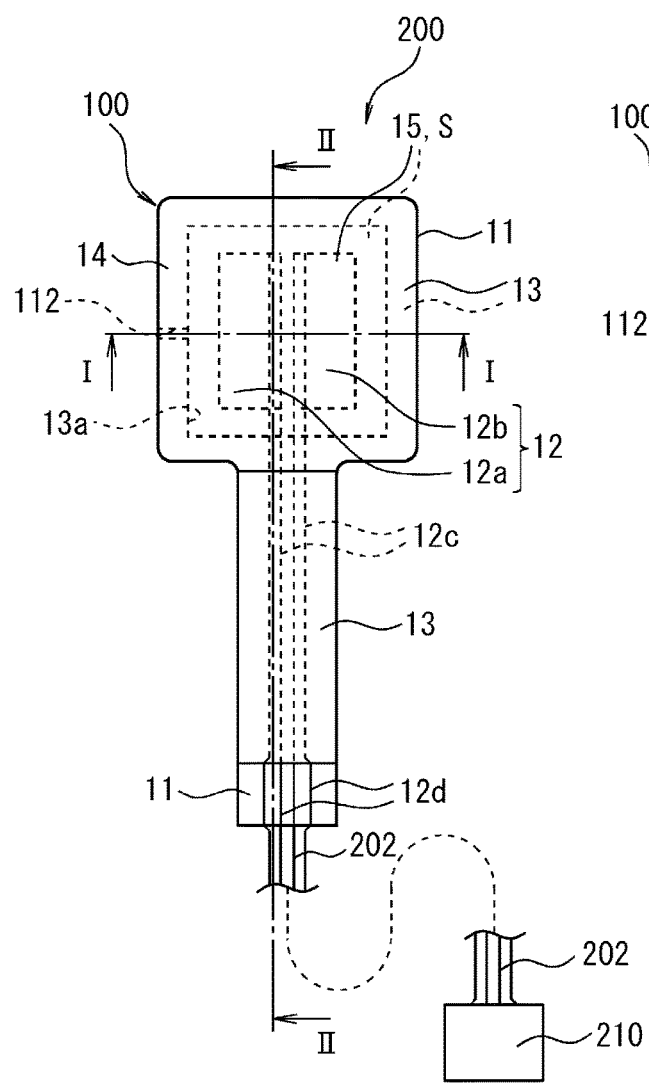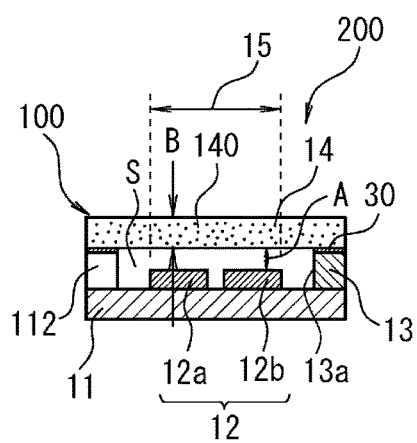

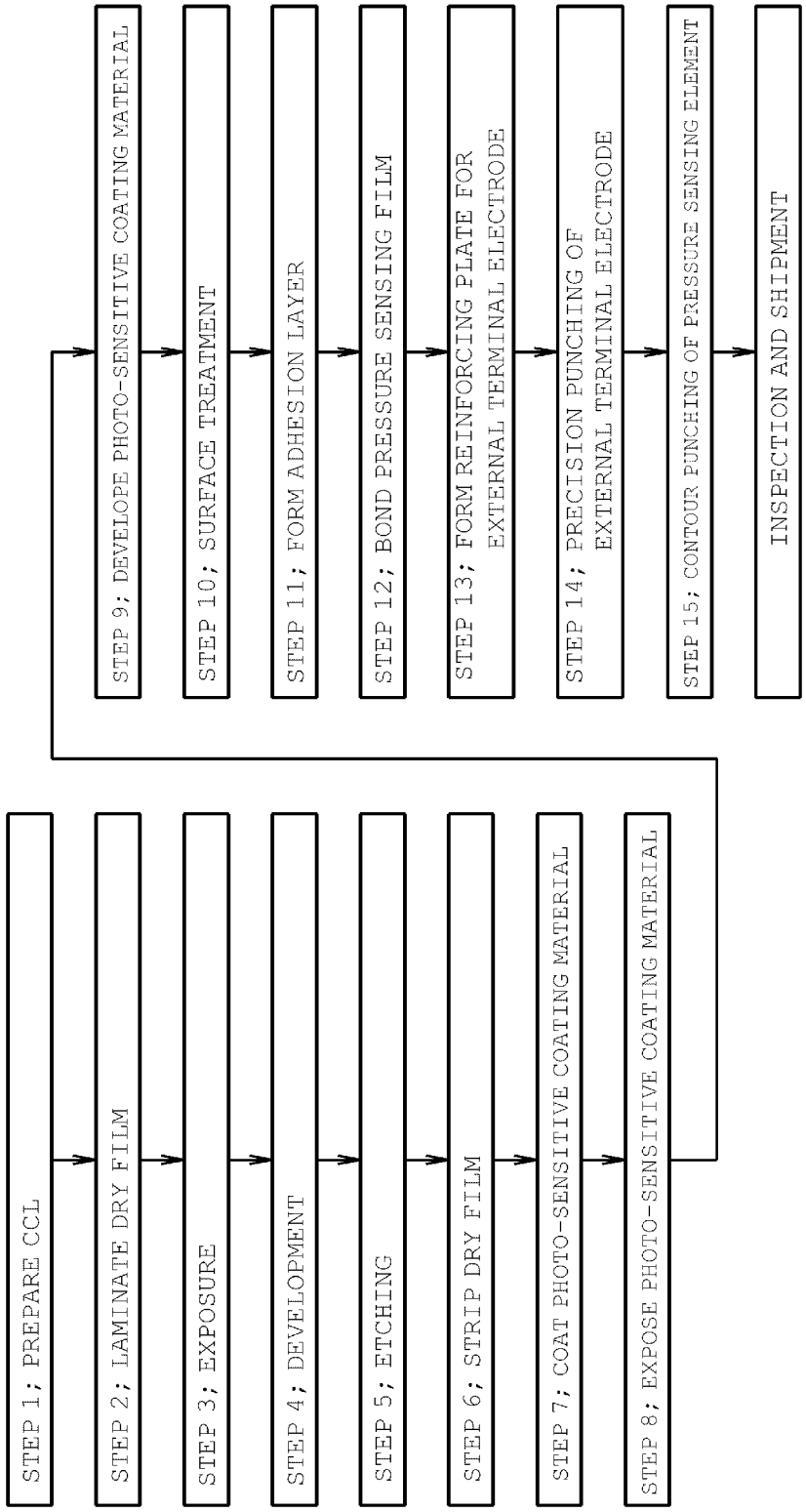

PRESSURE SENSING ELEMENT AND PRESSURE SENSOR

TECHNICAL FIELD

This invention relates to a pressure sensing element, and a pressure sensor.

BACKGROUND ART

In recent years, tactile sensing has rapidly been expanding its presence in the fields of medical treatment, welfare, robot, virtual reality, and so forth.

In the automotive field, for example, it has been typical to embed a pressure sensing element into a seat. This is aimed at prompting a passenger who rides in a vehicle and sits on the seat to fasten a seat belt. More specifically, upon sitting of the passenger on the vehicle seat, a predetermined level or larger load (weight) is applied to the pressure sensing element. Accordingly, a pressure sensor equipped with the pressure sensing element senses the presence of the passenger, and prompts him or her to fasten the seat belt.

Other expected applications of the pressure sensor include those in medical or nursing field.

More specifically, for example, the pressure sensing element embedded in a mattress of a bed is expected to monitor how the weight of a patient or aged person (also referred to as patient, etc., hereinafter) is applied when he or she lies thereon. By the monitoring, it becomes possible to detect that the patient, etc. has been lying on bed in a fixed posture for a long time. Again by the monitoring, a third party can know when to suitably change the posture of the patient, etc. lying on bed, for bedsore prevention.

It is also possible to use the pressure sensor for a walking aid of the patient, etc. More specifically, if an aged person, while waking with a waking aid, embedded with a pressure sensing element, should lose his or her balance, the pressure sensor can detect the unbalanced weight of the aged person as a change in pressure distribution. It is therefore expected to provide falling prevention for the aged person, or detection of falling.

A conventional pressure sensing element, having been widely known, is embodied to have an electro-conductive pressure sensitive resistor formed on a flexible film such as resin film, and a sensor electrode provided so as to oppose with the pressure sensitive resistor. The pressure sensing element of this embodiment is preferred since it is less likely to make the user feel uncomfortable when touched. Specific examples are exemplified by those described in Patent Literatures 1 to 4. Each of the pressure sensing elements disclosed in Patent Literatures 1 to 4 has a pressure sensitive resistor formed on a resin film by printing an electro-conductive material. The pressure sensitive resistor formed by printing is referred to as "pressure sensitive resistor I", hereinafter.

Patent Literature 1 discloses a pressure sensitive sensor having a film-like pressure sensitive resistor formed by coating an ink composition by printing, and then drying, on a film of polyethylene terephthalate or the like, wherein the ink composition is obtained by dissolving and dispersing an electro-conductive particle, an elastomer particle and a binder into a solvent.

Patent Literature 2 discloses a pressure sensor having a pressure sensitive resistor formed by coating a pressure sensitive resistor paste on a film of polyethylene terephthalate, polyether imide or the like, wherein the paste contains a base polymer, an electro-conductive material such as carbon black, and a filler.

Patent Literature 3 discloses a surface pressure distribution sensor having an opposing electrode film which is composed of a polyethylene terephthalate or polyethylene naphthalate film, and an evaporated pressure sensitive resistor (electro-conductive film) made of gold (Au) or other metal formed on the back surface thereof.

Patent Literature 4 discloses a pressure sensor sheet having a pressure sensitive resistor which is formed by coating a material, obtained by dispersing carbon into a thermosetting resin, onto a base film by screen printing.

Patent Literature 5 discloses a pressure sensor having a pressure sensing part which is configured by a cover film composed of a polyimide film, and a pressure sensitive resistor (pressure sensing film) containing copper oxide or the like formed thereon. This literature describes methods of forming the pressure sensitive resistor, including a method of depositing copper oxide or the like by sputtering or evaporation onto the polyimide film, and a method of oxidizing a copper foil laminated on the polyimide film to thereby convert the surface thereof into copper oxide. The pressure sensitive resistor formed by sputtering, evaporation or the like will also be referred to as "pressure sensitive resistor II", hereinafter.

CITATION LIST

Patent Literature

[Patent Literature 1] JP-A-2002-158103
[Patent Literature 2] JP-A-2001-159569
[Patent Literature 3] JP-A-2003-344195
[Patent Literature 4] JP-A-2004-028883
[Patent Literature 5] JP-A-2012-247372

SUMMARY OF THE INVENTION

Technical Problem

However, the pressure sensitive resistors I described in Patent Literatures 1 to 4 do not demonstrate sufficient levels of durability against deformation caused by repetitive bending, bending with a very small bend radius, or large load such as human weight. This is a problem specific to the members formed by printing. That is, the pressure sensitive resistor I is likely to crack by repetitive use or excessive bending. The cracked pressure sensitive resistor I may at worst disconnect the wiring, and may fail to generate output from the sensor. The pressure sensitive resistor I is therefore difficult to stably demonstrate a good electrical reliability over a long period. The pressure sensitive resistor I may also cause dropping of the electro-conductive particle after repetitive contact with the sensor electrode. The dropped electro-conductive particle may act as an electro-conductive foreign matter, to cause short-circuiting and erroneous detection by the pressure sensor.

The pressure sensitive resistor II described in Patent Literature 5 has a very small film thickness as compared with the pressure sensitive resistor I, due to specialty of method of manufacturing, so that production of pinholes is inevitable in the process of manufacturing. Accordingly, the pressure sensitive resistor II may occasionally be poor in electrical reliability. The pressure sensitive resistor II, in the form of thin film, may also wear, crack and then degrade after repetitive contact with the sensor electrode.

This invention was conceived in consideration of the problems described above. This invention is to provide a pressure sensing element configured to be flexible, and capable of demonstrating a stable electrical reliability over a long period; and, a pressure sensor having such pressure sensing element.

Solution to Problem

The pressure sensing element of this invention characteristically includes: an electro-conductive pressure sensing film; a sensor electrode provided at a position faced to the pressure sensing film; and an insulating layer which creates a predetermined distance between the pressure sensing film and the sensor electrode so as to keep them apart from each other. The pressure sensing film is a resin film containing carbon particles.

The pressure sensor of this invention characteristically includes: the pressure sensing element of this invention; and a detection unit which is electrically connected with the pressure sensing element so as to detect contact resistance between the pressure sensing film and the sensor electrode.

Advantageous Effects of Invention

The pressure sensing element of this invention, having a pressure sensing film composed of a resin film which discretely contains the carbon particles mixed therein, demonstrates a stable electrical reliability over a long period, while being flexible.

The pressure sensor, having the highly flexible pressure sensing element, is also suitably applicable to technical fields where bending is necessary, and can demonstrate a good tactile sensing over a long period, as a result of good electrical reliability of the pressure sensing element.

BRIEF DESCRIPTION OF DRAWINGS

The above and other objects, features and advantages of this invention will be more apparent from the following description of certain preferred embodiments taken in conjunction with the accompanying drawings.

FIG. 1 (a) is a plan view illustrating a pressure sensor according to a first embodiment of this invention, and (b) is a cross-sectional view taken along line I-I in (a).

FIG. 10 A flow chart of steps of manufacturing the pressure sensing element according to the first embodiment of this invention.

DESCRIPTION OF EMBODIMENTS

Embodiments of this invention will now be explained referring to the attached drawings. In all drawings, all similar constituents will be given the same reference signs to suitably avoid repetitive explanation.

The various constituents of this invention are not always necessarily be independent entities, instead allowing typically that a plurality of constituents are formed as a single member, that a single constituent is formed by a plurality of members, that one constituent forms a part of other constituent, and that a part of one constituent overlaps a part of other constituent.

In this specification, "initial state" means a state where the pressure sensing film stays unpressurized from outside. "Dynamic range" means a variable range of contact resistance between the sensor electrode and the pressure sensing film. "Initial detection sensitivity" means sensitivity with which the initial pressure sensing load is detected. "Initial pressure sensing load" means a minimum pressurizing force under which electrical conduction in the sensor electrode is detectable, when the pressure sensing film is pressurized from outside, and the pressure sensing film and the sensor electrode are brought into contact. Now "electrical conduction is detectable" means either that current or voltage not smaller than a predetermined threshold value is detected, or that current or voltage exceeding zero is substantially detected. The smaller the initial pressure sensing load, the higher the initial detection sensitivity, whereas the larger the initial pressure sensing load, the lower the initial detection sensitivity. In most cases, the initial detection sensitivity preferably falls within a predetermined range. This is because, the detection will be insufficient if the initial detection sensitivity is too low, meanwhile even a very small load unintended for detection may be detected to cause erroneous detection if the initial detection sensitivity is too high.

<First Embodiment>

Figure 2A:
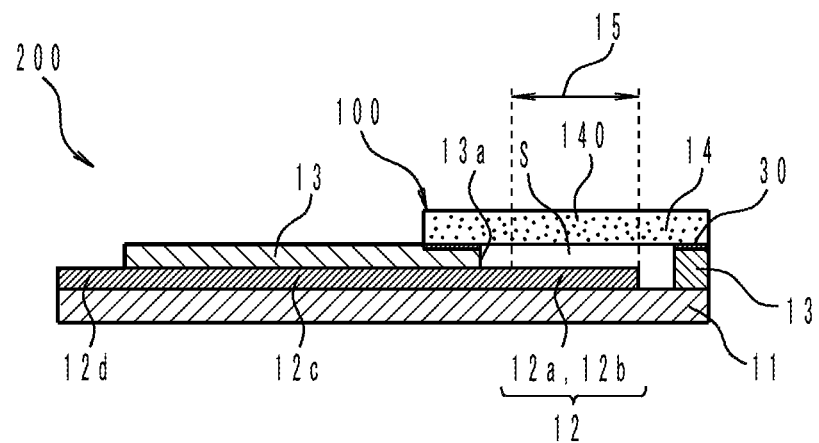
FIG. 2 (a) is a cross-sectional view taken along line II-II in FIGS. 1(a), and (b) is a modified example of the cross-sectional view taken along line II-II in FIG. 1(a).
Figure 2B:
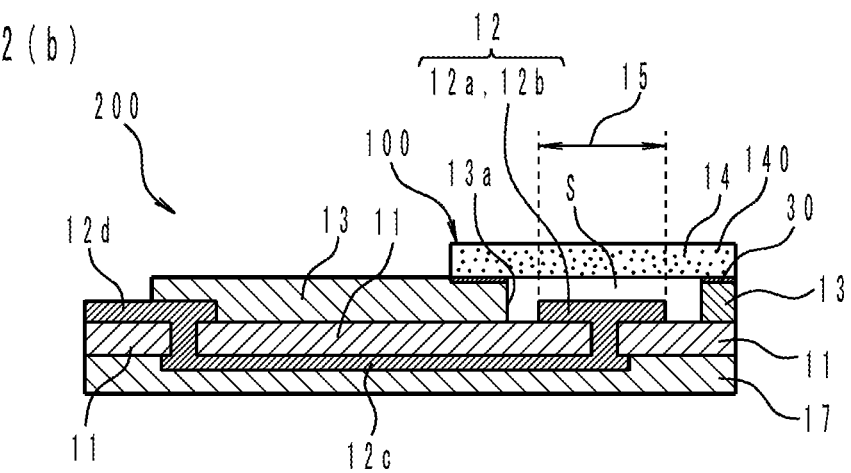
Figure 3A:
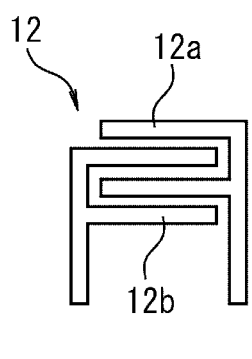
FIG. 3 (a) to (c) are plan views illustrating modified examples of the sensor electrode.
Figure 3B:
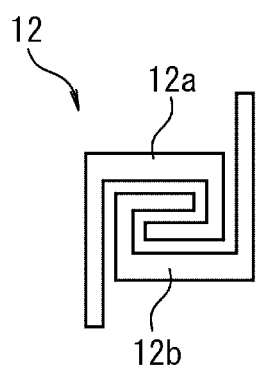
Figure 3C:
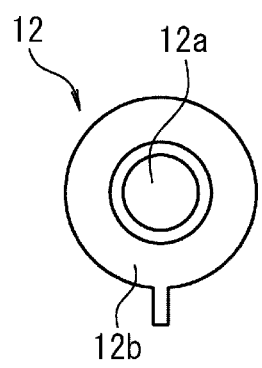
Figure 4:
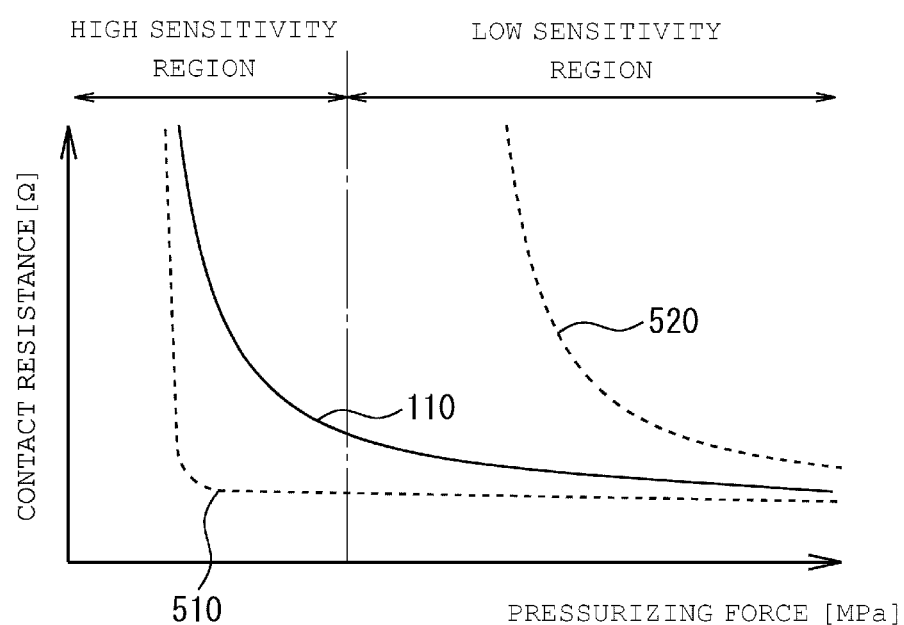
FIG. 4 An explanatory drawing explaining initial detection sensitivity and dynamic range of the pressure sensing element of the first embodiment.

A pressure sensing element and a pressure sensor of the first embodiment will be explained below, referring to FIG. 1 to FIG. 4, and FIG. 10. FIG. 1(a) is a plan view illustrating a pressure sensor 200 according to the first embodiment of this invention. FIG. 1(b) is a cross sectional view taken along line I-I in FIG. 1(a). FIG. 2(a) is a cross sectional view taken along line II-II in FIG. 1(a), and FIG. 2 (b) is a modified example of the cross-sectional view taken along line II-II in FIG. 1(a). FIG. 3(a) to FIG. 3(c) are plan views illustrating modified examples of a sensor electrode 12. FIG. 4 is an explanatory drawing explaining the initial detection sensitivity and dynamic range of a pressure sensing element 100 (see FIG. 1) of the first embodiment. A curve 110 illustrated in FIG. 4 merely indicates a tendency of the dynamic range of the pressure sensing element 100, without limiting this invention. FIG. 10 is a flow chart of steps of manufacturing the pressure sensing element 100 of the first embodiment.

The pressure sensing element 100 of this embodiment is a single-channel type element configured by a pressure sensor part 15 having a single sensor electrode 12 and a pressure sensing film 14 opposed to each other.

First, the pressure sensing element 100 and the pressure sensor 200 of this embodiment will be outlined.

As illustrated in FIG. 1, the pressure sensing element 100 has the electro-conductive pressure sensing film 14, the sensor electrode 12 provided at a position faced to the pressure sensing film 14, and an insulating layer 13 which creates a predetermined distance "A" between the pressure sensing film 14 and the sensor electrode 12 so as to keep them apart from each other. The pressure sensing film 14 is a resin film containing carbon particles 140.

Meanwhile, as illustrated in FIG. 1(a), the pressure sensor 200 has the pressure sensing element 100 and a detection unit 210. The detection unit 210 is electrically connected to the pressure sensing element 100 so as to detect contact resistance between the pressure sensing film 14 and the sensor electrode 12.

The pressure sensing element 100 of this embodiment is a device, whose measurable physical quantity varies depending on load of pressurizing force from outside. The pressure sensing element 100 of this embodiment, when applied with pressurizing force, is varied in the contact resistance between the pressure sensing film 14 and the sensor electrode 12. The variable quantity in the contact resistance in the pressure sensing element 100 correlates with the pressurizing force, and the pressure sensor 200 can quantify the pressurizing force by quantitatively detecting the contact resistance. Now "quantitatively detecting the pressurizing force" includes not only continuous detection of the pressurizing force, but also stepwise detection of the pressurizing force under predetermined levels of load.

The pressure sensing film 14 is a film capable of electrically connected to the sensor electrode 12 when externally pressurized. Now "the pressure sensing film 14 is electorconductive" means that the pressure sensing film 14, when externally pressurized, shows an electro-conductivity enough to allow current to flow therethrough, so as to electrify the sensor electrode 12. Although not illustrated, the pressure sensing element 100 may optionally be equipped with a voltage applying unit for applying voltage to the sensor electrode 12.

The pressure sensor 200 of this embodiment is a variable resistance sensor making use of change in the contact resistance in principle, and is a distribution sensor capable of continuously detecting pressure.

As described above, the pressure sensing film 14 is a resin film, and is configured to be electro-conductive as a result of incorporation of a lot of carbon particles 140. The pressure sensing film 14 is, therefore, more flexible as compared with the conventional pressure sensitive resistors formed typically by printing, sputtering or evaporation on a film, highly durable to repeated use, and highly bendable. The pressure sensing film 14 will not drop the electro-conductive particles unlike the pressure sensitive resistor formed by printing, and has no pinholes unlike the film formed by evaporation or the like. The pressure sensing element 100 having such excellent pressure sensing film 14 is again excellent in the electrical reliability and durability.

The pressure sensing film 14 contains high-resistivity carbon particles as an electro-conductive material, and is composed of a resin film. The pressure sensing film 14 is, therefore, superior to the conventional pressure sensitive resistors I, II in terms of flexibility and film strength, and is less likely to crack even if bent or repetitively touched. Since the pressure sensing film 14 is composed of a resin film as described above, it may have a freely designed thickness and a high accuracy in the surface roughness. The pressure sensing film 14 may therefore be optimally designed, which has not been easy for the conventional pressure sensitive resistors formed by printing, evaporation or other techniques.

The pressure sensor 200 has the excellent pressure sensing element 100 described above, and can demonstrate high durability and electrical reliability, endowed by the pressure sensing element 100.

The detection unit 210 provided to the pressure sensor 200 suitably includes a power unit (not illustrated) for applying voltage to a voltage applying unit (not illustrated), and a processing unit (not illustrated) for calculating pressurizing force loaded onto the sensor electrode 12 through the pressure sensing film 14. The sensor electrode 12 in this embodiment is configured by combining a pair of first electrode 12a and second electrode 12b. When the sensor electrode 12 is applied with pressurizing force through the pressure sensing film 14, the first electrode 12a and the second electrode 12b are electrically connected, and current flows in a lead wire 12c.

Operation principle of the pressure sensor 200 is as follows. The first electrode 12a and the second electrode 12b illustrated in FIG. 1(a) are connected to an unillustrated current source. In the state where no pressurizing force is applied to the pressure sensing film 14, as illustrated in FIG. 1(b), the pressure sensing film 14 and the sensor electrode 12 are kept apart, and are not electrically connected. Although not illustrated, when the pressure sensing film 14 is externally loaded with the pressurizing force (from the upper side of drawing), the pressure sensing film 14 deflects towards the sensor electrode 12, comes into contact with the first electrode 12a and the second electrode 12b, and is electrified.

One excellent feature of the pressure sensing element 100 of this embodiment is depicted by a large variable range (also referred to as dynamic range) of the contact resistance between the sensor electrode 12 and the pressure sensing film 14, and a high initial detection sensitivity. In FIG. 4, a curve 110 indicates tendencies of the dynamic range and the initial detection sensitivity of the pressure sensing element 100 (see FIG. 1), whereas a curve 510 and a curve 520 indicate undesirable tendencies of the dynamic range and the initial detection sensitivity. The ordinate represents the contact resistance [Ω] between the pressure sensing film 14 and the sensor electrode 12, and the abscissa represents the pressurizing force [MPa]. The ordinate is given in a logarithmic scale.

As indicated by the curve 110, the pressure sensing element 100 may be designed so as to initially detect the pressurizing force in the high sensitivity region, with a sufficiently large dynamic range. Accordingly, the pressure sensing film 14, when externally touched, can successfully detect the load (pressurizing force), in a quantitative manner. The comparative curve 510 indicates a high initial detection sensitivity but only a small dynamic range. The comparative curve 520 indicates a large dynamic range but only a low initial detection sensitivity.

The reason why the curve 110 may successfully be achieved in this embodiment is that the pressure sensing film 14 is composed of a resin film, and that the carbon particles 140 are selected as a material for imparting electro-conductivity to the pressure sensing film 14. Accordingly, it will be easy to design the pressure sensing film 14, containing a proper amount of high-resistivity carbon particles 140 as an electro-conductive material, so that the surface resistivity of the pressure sensing film 14 falls in a desirable range. Since the pressure sensing film 14 is composed of a resin film, it has a high flexibility, and can sensitively detect the initial pressurizing force. This is why the good initial detection sensitivity is indicated by the curve 110. In addition, as the pressurizing force externally loaded onto the pressure sensing film 14 increases, the amount of deflection of the pressure sensing film 14 increases, and thereby the area of contact between the sensor electrode 12 and the pressure sensing film 14 continuously increases. In this way, the pressure sensing film 14 successfully achieves a large dynamic range.

The larger the pressurizing force loaded onto the pressure sensing film 14, the smaller the contact resistance between the sensor electrode 12 and the pressure sensing film 14. The current value of the lead wire 12c increases as a consequence. Based on the current value, the unillustrated processing unit provided to the detection unit 210 quantitatively estimates the pressurizing force loaded onto the sensor electrode 12. The pressure sensing element 100 of this embodiment may therefore be used as the pressure sensor 200.

The pressure sensor 200 of this embodiment may be configured as a device which quantitatively detects the pressurizing force externally loaded and makes output. Information regarding result of detection, which may be output from the pressure sensor 200, includes distribution of the pressurizing force or surface pressure, or other physical quantity which can be converted therefrom, without special limitation. For example, the surface pressure detected by the pressure sensor 200 may be converted to flow rate of air or water which collides on the pressure sensor 200, and then output.

Next, pressure sensing element 100 of this embodiment will be detailed.

As illustrated in FIGS. 1 (*a*), (b), the pressure sensing element 100 of this embodiment has the support substrate 11 which supports the sensor electrode 12. On one surface of the support substrate 11, there is formed the sensor electrode 12, and there are stacked the insulating layer 13 having an opening 13a formed therein, and the pressure sensing film 14. The sensor electrode 12 is arranged inside the opening 13a. The insulating layer 13 and the sensor electrode 12 are provided on the upper face of the support substrate 11. The maximum thickness of the insulating layer 13 is larger than the maximum thickness of the sensor electrode 12. More specifically, in this embodiment, the sensor electrode 12 and the insulating layer 13 are provided on the same plane, and the thickness of the insulating layer 13 is larger than the thickness of the sensor electrode 12. The pressure sensing film 14 is stacked over the support substrate 11 while placing the insulating layer 13 in between, so that the pressure sensing film 14 and the sensor electrode 12 are spaced from each other by a difference of thickness between the insulating layer 13 and the sensor electrode 12. In other words, the insulating layer 13 serves as a spacer for spacing the sensor electrode 12 the pressure sensing film 14 by a predetermined distance "A" (see FIG. 1 (*b*)). In the initial state without being externally applied with pressurizing force, the sensor electrode 12 and the pressure sensing film 14 are kept apart, so that the sensor electrode 12 is not electrified. The pressure sensor part 15 is configured by the sensor electrode 12 and the pressure sensing film 14 opposing thereto.

As illustrated in FIGS. 1 (*a*), (b) and FIGS. 2 (*a*), (b), inside the pressure sensing element 100, there is formed a hollow space S surrounded by the support substrate 11, the insulating layer 13, and the pressure sensing film 14. The insulating layer 13 may optionally have formed therein a vent hole 112 through which the hollow space S and the outside of the pressure sensing element 100 can communicate (see FIGS. 1 (*a*), (b)). With the vent hole 112, the pressure sensing element 100 can clear the difference between the inner pressure of the hollow space S and the external pressure. While the widthwise dimension of the vent hole 112 is not specifically limited, when given a widthwise dimension of 50 μm or larger and 500 μm or smaller, the vent hole 112 can fully demonstrate the pressure control function. While the height of the vent hole 112 is again not specifically limited, when given a height equivalent to the thickness of the insulating layer 13, the vent hole 112 can be formed at the same time with the opening 13a, taking an advantage in terms of productivity. Alternatively, the insulating layer 13, when configured with a highly breathable insulating material, can demonstrate such pressure control function without being provided with the vent hole 112.

In this embodiment, membrane, sheet and film are synonymous and are not discriminative, and embrace so-called panel and plate.

The pressure sensing film 14 is a component which is brought into contact with the sensor electrode 12, to electrify the pair of the first electrode 12a and the second electrode 12b, which configure the sensor electrode 12. More specifically, the pressure sensing film 14 which is externally loaded by pressurizing force is brought into contact with the first electrode 12a and the second electrode 12b so as to bridge them, and thereby the first electrode 12a and the second electrode 12b are electrically connected.

The pressure sensing film 14 is composed of a resin film containing the carbon particles 140. Since the pressure sensing film 14 is a resin film having electro-conductivity, and configures a pressing area, so that the pressure sensing film 14 is less likely to make the user, who externally touches it, feel foreign matter sensation.

The sensor electrode 12 is electrified by elastic deformation of the pressure sensing film 14 externally loaded with pressurizing force. Since being composed of a flexible resin film, the pressure sensing film 14 is prevented from cracking even after repetitive use (touch).

In the pressure sensing element 100, the predetermined distance "A", measured in the initial state while keeping the pressure sensing film nearly flat, is preferably 5 μm or longer and 25 μm or shorter. With the distance "A" being 5 μm or longer, it is feasible enough, in the initial state, to avoid contact and short-circuiting between the pressure sensing film 14 and the sensor electrode 12, even if the pressure sensing element 100 is bent or curved. Meanwhile, with the distance "A" being 25 μm or shorter, the pressure sensing element 100 will not be degraded in the initial detection sensitivity.

Now the "initial state" means a state where the pressure sensing film 14 stays unpressurized from outside.

The pressure sensing film 14 in this embodiment is a single filmy matter faced to the pair of first electrode 12a and second electrode 12b.

In the pressure sensing element 100 of this embodiment, when stays in the initial state without being pressurized, the pressure sensing film 14 and the sensor electrode 12 are kept apart, without being brought into contact, by the insulating layer 13. Accordingly, upon loaded by the pressurizing force to bring the pressure sensing film 14 and the sensor electrode 12 into contact, the area of contact may be varied over a wide range from zero up to the whole area of the sensor electrode 12. The contact resistance between the pressure sensing film 14 and the sensor electrode 12 may therefore be reduced to a considerable degree. The amount of increase in the contact area between the pressure sensing film 14 and the sensor electrode 12 positively correlates with the amount of decrease in the contact resistance. Since the pressure sensing film 14 is a resin film containing the carbon particles 140, further increase in the pressurizing force will further improve the state of contact in the contact portion already established, and thereby the contact resistance will further decrease. Now the contact portion includes a portion where the carbon particles 140 which distribute near the surface of the pressure sensing film 14 come into contact with the sensor electrode 12; and a portion where the adjacent ones of the plurality of carbon particles 140 contained in the pressure sensing film 14 come into contact to each other. In other words, in the pressure sensing element 100 of this embodiment, the contact resistance is reduced by a synergistic effect of a macro factor represented by increase in the contact area and a micro factor represented by improvement in the state of contact. In this way, by making use of such large variation in resistivity correlated to the magnitude of pressurizing force, the pressurizing force may be detected with high accuracy. In short, the pressure sensing element 100 is characterized by a large dynamic range, as illustrated in FIG. 4.

The resin film composing the pressure sensing film 14 may be configured suitably by using known resins, without departing from the spin of this invention. The resins are specifically exemplified by polyesters such as polyethylene terephthalate and polyethylene naphthalate; cyclic polyolefin; polycarbonate; polyimide; polyamide-imide; and liquid crystal polymer. Any one species of these resins, or a plurality of species of them may be used to configure the pressure sensing film 14.

The pressure sensing element 100 is preferably configured using the pressure sensing film 14 having a heat resistant temperature of 260° C. or above. By configuring the pressure sensing element 100 using a member having such high heat resistance, the pressure sensor 200 having the pressure sensing element 100 incorporated therein becomes adoptable to reflow process. This consequently expands a range of components adoptable to the pressure sensor 200, to thereby also expand ranges of application and specification of the pressure sensor 200.

From the viewpoint of heat resistance, the resin composing the pressure sensing film 14 preferably contains polyimide or polyamide-imide as a main ingredient. Polyimide and polyamide are superior to polyethylene terephthalate and other general-purpose resins, in terms of heat resistance. More specifically, the resin film which contains polyimide or polyamide-imide as a main ingredient possibly shows a heat resistance temperature of 260° C. or above. Now the main ingredient means a resin which accounts for 50% by mass or more, preferably 70% by mass or more, and particularly 90% by mass more, relative to 100% by mass of the resin composing the pressure sensing film 14. For example, as the resin contained in the pressure sensing film 14, either polyimide or polyamide-imide, or a combination thereof may substantially account for 100% by mass.

Next, the carbon particle 140 contained in the pressure sensing film 14 will be explained. The carbon particle 140 is a component which makes the pressure sensing film 14 electro-conductive. The carbon particle 140 is a particulate carbon material, and is any single species of, or combination of two or species of carbon blacks such as acetylene black, furnace black (Ketjen black), channel black and thermal black; and graphite, but not limited thereto.

The content of the carbon particle 140 in the pressure sensing film 14, and shape and particle size of the carbon particle 140 are not specifically limited without departing from the spirit of this invention. They are suitably determined, so long as the sensor electrode 12 may be electrified, corresponding to the contact resistance between the pressure sensing film 14 and the sensor electrode 12.

Referring now back to the description above, the conventional pressure sensing elements have been configured so that a pressure sensing portion, having a resin film and a pressure sensitive resistor formed thereon by printing, is opposed to a sensor electrode. This enabled only poor levels of accuracy in controlling the thickness of the pressure sensing portions, and the roughness of the surface thereof faced to the sensor electrode. In contrast, in the pressure sensing element 100 in this embodiment, the resin film containing carbon particles per se configures the pressure sensing film 14, so that the thickness of the film and the roughness of the surface thereof faced to the sensor electrode 12 are precisely controlled. The film thickness and the surface roughness of these levels contribute to uniformity of the contact resistance of the pressure sensing film 14 with respect to the sensor electrode 12. The pressure sensing element 100 thus ensures a stable sensor output and a high electrical reliability. The pressure sensing element 100 also makes it possible to configure the portion, having conventionally been configured using a resin film and a pressure sensitive resistor formed on the surface of the resin film, by using the resin film only. This contributes to thin the portion. By thinning the portion, the user will become less likely to feel foreign matter sensation on the pressure sensing element 100, and the pressure sensing element 100 will more easily be disposed along curved surface.

More specifically, the pressure sensing film 14 preferably has a thickness of 6.5 μm or larger and 40 μm or smaller. With the thickness controlled to 6.5 μm or larger, the pressure sensing film 14 remains durable. Meanwhile, with the thickness controlled to 40 μm or smaller, the pressure sensing film 14 will show a good initial detection sensitivity when pressurized, while keeping a large dynamic range.

The thickness of the pressure sensing film 14 may be measured using popular thickness measuring means such as height gauge, upright gauge and so forth.

The pressure sensing film 14 preferably has a surface resistivity of 7 kΩ/sq or larger and 30 kΩ/sq or smaller. With the surface resistivity controlled in the above descried range, the pressure sensing film 14 will show only a small variation in the sensed resistivity when loaded with a large load, proving a high electrical reliability. Now, the large load is roughly estimated as 1.1 MPa or around (for example, a pressurizing force of 450 gf is applied to the pressure sensor part 15 having an area of 4 mm$^2$).

With the surface resistivity controlled in the above described range, it becomes now possible to achieve a good initial detection sensitivity and a large dynamic range, as indicated by the curve 110 in FIG. 4. More specifically, the pressure sensing element 100 may be designed to show an initial detection sensitivity of 0.25 MPa or smaller, even in higher sensitivity region typically at 0.17 MPa or below, and can show gradated changes in the sensor output ranging from the initially detectable load of pressurization up to the maximum load.

The desired level of surface resistivity of the pressure sensing film 14 may be controlled based on the content of the carbon particles 140 to be contained in the pressure sensing film 14. In other words, the content of carbon particles 140 in the pressure sensing film 14 may be determined, aiming that the surface resistivity of the pressure sensing film 14 falls in the above-described range.

In a filmy matter such as pressure sensing film 14, electric current mainly flows through the surficial portion of that filmy matter. Therefore in this specification, resistivity of the filmy matter is defined by the unit of sheet resistance per unit area, ignoring the thicknesswise dimension, specifically denoted by using Ω/□ or Ω/sq.

The pressure sensing element 100 may be conditioned so that the surface of the pressure sensing film 14 faced to the sensor electrode 12 will have a surface roughness Rz of 0.10 μm or larger and 0.50 μm or smaller. In this manner, the pressure sensing film 14 is formed with such good film property, and the sensitivity of detecting the contact resistance may be stabilized.

The surface roughness Rz of the pressure sensing film 14 is measured using some popular surface roughness tester, or by surface roughness analysis under a laser microscope. The popular surface roughness tester is exemplified by four-probe analyzer, and more specifically exemplified by, but not limited to, a resistivity meter available from Mitsubishi Chemical Analytech Co., Ltd.

From the viewpoint of suitably expanding the dynamic range, the pressure sensing film 14 preferably has a Young's modulus of 5 GPa or smaller. This successfully makes the pressure sensing film 14 flexible enough, and thereby the contact resistance may suitably be quantified as the pressure sensing film 14 is increasingly loaded with the pressurizing force.

In particular, the pressure sensing film 14 preferably has a thickness of 6.5 μm or larger and 40 μm or smaller, a Young's modulus of 5 GPa or smaller, and a predetermined distance "A" for keeping the pressure sensing film 14 and the sensor electrode 12 apart from each other of 5 μm or longer and 25 μm or shorter. The pressure sensing element 100, provided with thus embodied pressure sensing film 14, can prevent short-circuiting of the sensor electrode 12 in the initial state even if disposed along a curved surface given by a small radius of curvature, show a good initial detection sensitivity, and show a large dynamic range. In short, this pressure sensing element 100 is suitably used, when mounted on a curved surface. The curved surface given by a small radius of curvature typically has a radius of curvature φ of 30 mm or smaller.

The Young's modulus of the above-described pressure sensing film 14 is typically smaller than the Young's modulus of a film of the same thickness, composed of the resin which composes the pressure sensing film 14.

For this embodiment, it is preferable for example to select polyimide or polyamide-imide as the resin for composing the pressure sensing film 14. The pressure sensing film 14 formed by adding carbon particles 140 to polyimide or the like tends to show the Young's modulus smaller than the Young's modulus of a film composed of polyimide resin or the like only. This tendency means that the pressure sensing film 14 has a distinctively improved flexibility, over the conventional pressure sensing portion configured by a resin film and a pressure sensitive resistor formed thereon. The pressure sensing element 100 can thus demonstrate a good initial detection sensitivity and a large dynamic range.

The pressure sensing film 14 in this embodiment may be manufactured by a method not specifically limited, and typically by mixing a single species, or two or more species of source resins with the carbon particles 140, followed by proper kneading and casting into a film.

Next, the sensor electrode 12 will be explained.

In this embodiment, the sensor electrode 12 is a pair of electrodes disposed side by side, and kept apart by a predetermined distance in the in-plane direction. The sensor electrode 12 is formed on the support substrate 11, according to a desired pattern. As illustrated in FIG. 1 (a), the sensor electrode 12 in this embodiment is configured by a rectangular first electrode 12a, and a second electrode 12b having substantially the same shape as the first electrode 12a, which are disposed side by side in parallel, and spaced by a predetermined distance. The pattern of the sensor electrode 12 is, however, not limited thereto, instead allowing that, as illustrated in FIG. 3 (a) and FIG. 3 (b), the first electrode 12a and the second electrode 12b have a comb-like pattern and a spiral pattern, respectively, which mesh with each other. Alternatively, as illustrated in FIG. 3(c), the first electrode 12a and the second electrode 12b may be arranged concentrically. More specifically, one of the first electrode 12a and the second electrode 12b has a circular pattern, and the other has a ring pattern surrounding the circular pattern while keeping a predetermined distance in between. The circular pattern includes perfect circle, ellipse and oblong circle patterns.

The space between the opposed first electrode 12a and the second electrode 12b is not specifically limited. For example, if the predetermined distance "A" between the sensor electrode 12 and the pressure sensing film 14 is 5 μm or larger and 25 μm or smaller, a desired pressure sensing characteristic and stability of manufacture will be well balanced, by determining a design value of the distance as 50 μm or larger and 500 μm or smaller.

The sensor electrode 12 is configured using an electro-conductive member. In this embodiment, the sensor electrode 12 is configured by a low-resistivity metal material. In this embodiment, the surface resistivity of the sensor electrode 12 is smaller than the surface resistivity of the pressure sensing film 14. More specifically, the sensor electrode 12 is preferably composed of, but not limited to, copper, silver, copper- or silver-containing metal material, or aluminum. The form of material is suitably selectable from foil, paste and so forth, depending on a method of manufacturing the sensor electrode 12 to be combined.

The method of manufacturing the sensor electrode 12 is not specifically limited. For example, the sensor electrode 12 is manufactured by patterning a CCL (Copper Clad Laminate) into the first electrode 12a and the second electrode 12b, by photolithographic and etching techniques. Also the lead wire 12c or an external terminal electrode 12d may be formed at the same time in the patterning. The CCL used here is any of a laminate configured by bonding a copper foil, having a desired thickness, to the support substrate 11 using an adhesive or tacky agent; a laminate configured by casting or coating a varnish of an insulating resin onto a copper foil; and a laminate configured by forming a copper foil by wet plating onto the support substrate 11. While the thickness of the copper foil used in the above-described process is not specifically limited, with the thickness selected within the range from 9 μm or larger and 35 μm or smaller, which is a typical range having been used in the technical field of flexible printed circuit (FPC), the sensor electrode 12 will have a good finish.

From the viewpoint of dimensional accuracy in the thickness or width of the sensor electrode 12, and sensor output characteristic, the above-described sensor electrode 12 composed of the copper foil is preferable. Material for composing the sensor electrode 12 is however not limited to a copper foil, so long as the material can be electrically connected with the pressure sensing film 14 when brought into contact therewith. For example, aluminum foil, silver paste and so forth are usable as the material.

It is preferable that the thus manufactured sensor electrode 12 is further plated in a predetermined region thereof. More specifically, the surface of the sensor electrode 12, faced to the pressure sensing film 14, is plated. By the plating, the sensor electrode 12 may be prevented from being oxidized or degraded, and may be improved in the wear resistance against the pressure sensing film 14 which is repetitively pressed thereon. The plating may be given during, or succeeding to, the film making process of the sensor electrode 12. The plating is specifically exemplified by, but not limited to, nickel plating with a thickness of approximately 2 μm or larger and 10 μm or smaller, and gold plating with a thickness of approximately 0.02 μm or larger and 0.20 μm or smaller.

To the first electrode 12a and the second electrode 12b, the lead wires 12c are respectively connected. The lead wires 12c in this embodiment are formed integrally with the first electrode 12a and the second electrode 12b, and are drawn out to the external terminal electrodes 12d. The external terminal electrodes 12d are connected via a flexible wiring 202 to the detection unit 210.

The lead wires 12c in this embodiment are formed, as illustrated in FIG. 2(a), on the same surface of the support substrate 11 on which the sensor electrode 12 is formed. In other embodiment of the lead wires 12c, as illustrated in FIG. 2(b), apart of, or all of, the lead wires 12c may be once drawn out through a through hole (TH) onto the surface of the support substrate 11, which is opposite to the surface having the sensor electrode 12 formed thereon. The lead wires 12c drawn out onto the opposite surface are again drawn out, just in front of the external terminal electrode 12d, through a through hole onto the surface having the sensor electrode 12 formed thereon. Such double-sided board, having the lead wires 12c disposed on both sides thereof, is advantageous in terms of effective use of the space in the support substrate 11, and downsizing of the pressure sensor 200. The double-sided board can also cope with complication of the lead wires 12c, when a plurality of sensor electrodes 12 are provided on a single support substrate 11 to configure a so-called pressure sensor array. The double-sided board illustrated in FIG. 2 (b) has a cover 17 provided so as to cover and protect the lead wires 12c drawn out onto the opposite surface. The cover 17 is exemplified by, but not limited to, resin cover film typically used as a protective film.

Over the support substrate 11, the insulating layer 13 is stacked. The insulating layer 13 has the opening 13a which houses the sensor electrode 12. As illustrated in FIG. 1 (a) and FIG. 2 (a), the insulating layer 13 covers and protects the nearly entire surface of the support substrate 11 and the lead wires 12c (see FIG. 2), excluding the region where the sensor electrode 12 is formed and the peripheral region, to thereby improve the environmental resistance.

In the initial state where no pressurizing force is externally loaded onto the pressure sensing film 14, the insulating layer 13 serves as a spacer which keeps the sensor electrode 12 and the pressure sensing film 14 apart. The insulating layer 13 is composed of a sheet or paint having a photo-sensitive base material. After covering the support substrate 11, the sensor electrode 12 and the lead wires 12c with the insulating material, the insulating material is then processed by exposure and development, thereby the opening 13a is formed. By using a photo-sensitive material as the insulating material, the opening 13a is formed in the insulating layer 13 in a precise manner both in terms of dimension and position. Alternatively, a tacky sheet or adhesive sheet, having the opening 13a preliminarily formed therein, may be bonded to the upper face of the support substrate 11.

The photo-sensitive material is exemplified by an epoxy-base resin given an appropriate level of flexibility by a known technique such as urethane modification. By using such epoxy-based resin, the insulating layer 13 having an appropriate level of flexibility and heat resistance durable against reflow process, may be formed.

The height of the insulating layer 13, measured from the surface of the support substrate 11, is preferably designed to be in the range from 15 μm or larger and 70 μm or smaller, and more preferably from 15 μm or larger and 40 μm or smaller. By limiting the height of the insulating material to 70 μm or smaller, light which is illuminated in the process of exposure for forming the opening 13a can reach deep inside the photo-sensitive material, and thereby the opening 13a may be formed accurately. In order to further improve the exposure sensitivity in the process of forming the insulating layer 13, the photo-sensitive material is preferably given in a semi-transparent form, having a total light transmittance of 30% or larger. In the process of forming the opening 13a, also a vent hole 112 may optionally be formed.

As illustrated in FIG. 1 (b) and FIG. 2(a), the pressure sensing film 14 is provided so as to be brought into contact with the upper face (the surface on the side opposite to the support substrate 11) of the insulating layer 13. It is preferable, for example, to select the height of the insulating layer 13 in the above-described range, and to select to the height of the sensor electrode 12, formed on the same surface, in the range from 15 μm or larger and 45 μm or smaller. In this way, it now becomes possible to easily adjust the predetermined distance "A" (see FIG. 1 (b)), to be kept between the sensor electrode 12 and the pressure sensing film 14, to 5 μm or longer and 25 μm or shorter. Now the predetermined distance "A" is the distance measured from the upper face of the sensor electrode 12 to the bottom face of the pressure sensing film 14. Now, "upper" and "lower" in this context mean the directionality when the support substrate 11 is placed lower, and the pressure sensing film 14 is placed upper. With the predetermined distance "A" controlled within the range from 5 μm or longer and 25 μm or shorter, the pressure sensing element 100 will be prevented from causing short-circuiting in the initial state, even if the pressure sensing element 100 is bent or curved.

The opening 13a in this embodiment has a rectangular shape as illustrated in FIG. 1 (a). However, the shape of the opening 13a may suitably be altered to circular, polygonal or undefined shape, depending on the shape of the sensor electrode 12 housed therein.

As illustrated in FIG. 1 (b) and FIG. 2 (a), over the insulating layer 13, the pressure sensing film 14 is laminated. In this embodiment, the insulating layer 13 and the pressure sensing film 14 are bonded while placing an adhesion layer 30 in between. Which one of tacky agent, adhesive, tacky sheet and adhesive sheet may be used for the adhesion layer 30, so long as it can bond the insulating layer 13 and the pressure sensing film 14. The adhesion layer 30 preferably has an aperture profile substantially same as that of the opening 13a, so as not to affect the contact resistance between the sensor electrode 12 and the pressure sensing film 14. For example, the adhesion layer 30 may be provided on either the insulating layer 13 or the pressure sensing film 14, and then bond the other onto the one under proper alignment.

Next, the support substrate 11 will be explained. The support substrate 11 is any suitable substrate so long as it can support the sensor electrode 12 in this embodiment. For example, while the film-like support substrate 11 is used in this embodiment, any suitable surface of an article having a form other than film may be used as the support substrate 11.

For example, the pressure sensing element 100 of this embodiment is configured so as to have a flexible substrate (support substrate 11), the sensor electrode 12 formed at least on one surface of the substrate (support substrate 11), and so that the pressure sensing element 100 per se is flexible. With such configuration, the pressure sensing element 100 may be mounted and used on a curved surface or peripheral surface. The support substrate 11 is typically an insulating component.

The support substrate 11 in this embodiment is a flexible and insulating film. Materials composing the insulating film are exemplified by, but not limited to, polyethylene, polyethylene terephthalate, polyethylene naphthalate, cycloolefin polymer, polycarbonate, aramid resin, polyimide, polyimide varnish, polyamide-imide, polyamide-imide varnish, and flexible sheet glass.

Taking high-temperature durability of the pressure sensor 200 in an environment of use into consideration, the materials for composing the support substrate 11 are more preferably exemplified by highly heat-resistant polycarbonate, aramid film, polyimide, polyimide varnish, polyamide-imide, polyamide-imide varnish and flexible sheet glass. If a soldering process is involved in the manufacture of the pressure sensor 200, the materials for composing the support substrate 11 are more preferably any of polyimide film, polyimide varnish film, polyamide-imide film and polyamide-imide varnish film. The thickness of the support substrate 11 typically falls in the range from 12.5 µm or larger and 50 µm or smaller, although not specifically limited. With the thickness exceeding 12.5 µm, the support substrate 11 will demonstrate a good durability in the process of manufacturing or during use of the pressure sensor 200, meanwhile with the thickness smaller than 50 µm, the support substrate 11 will demonstrate a good flexibility, allowing convenient use of the pressure sensing element 100 when mounted on a curved surface, or used in a bent form. The support substrate 11 may be a product preliminarily formed into a sheet as described above, or may be formed by casting or coating, for example, a polyimide-base insulating varnish typically onto a Cu foil as a material of the sensor electrode 12. From the viewpoint, for example, of improving both of the durability and high sensitivity characteristics of the pressure sensing element 100, the support substrate 11 is preferably designed to be thicker than the pressure sensing film 14.

The pressure sensor 200 equipped with the above-described pressure sensing element 100 is excellent in flexibility, high sensitivity characteristic and electrical reliability, and is versatile for various applications. For example, the pressure sensing element 100 may be attached to the surface of a suitable object, and may be used for simple measurement for sensing pressure exerted on the surface. In particular, the pressure sensing element 100 may be attached to a curved surface such as bent surface or spherical surface, to be subjected touch operation, and also may be made operable while being switched among various functions depending on magnitude of the pressurizing force. It is advantageous not only in that it allows touch operation on a two-dimensional plane like in the conventional touch panel, but also in that it is applicable to electronic whiteboard or electronic paper which is used as a user interface allowing three-dimensional input.

For example, the pressure sensor 200 may be used while bending the pressure sensing element 100 with a radius of curvature of 15 mm or smaller. In particular when both of the pressure sensing film 14 and the support substrate 11 are composed of flexible members, the pressure sensor 200 may also be applied to the surface of an object having such small radius of curvature.

The pressure sensing element 100 of the pressure sensor 200 may be used while being bent overall with a radius of curvature of 15 mm or smaller, or may be bent partially with a radius of curvature of 15 mm or smaller. The pressure sensor 200 is therefore applicable to complex curved surfaces including a surface having regularly repeated ups and downs in profile, and a surface having irregular ups and downs.

Next, the method of manufacturing the pressure sensing element 100 will be explained referring to FIG. 10. Note that the manufacturing method described below by no means limit this invention. Steps 1 to 15 below may appropriately be changed in order, may partially be omitted, or may partially be modified.

[Step 1] Preparation of CCL

A CCL is prepared. The CCL may suitably be pierced to form a guide hole, in preparation for alignment which may be necessary in the succeeding steps. The CCL has a copper foil formed over the support substrate 11.

[Step 2] Step of Laminating Dry Film

The above-prepared CCL is rinsed with an acid, and is laminated with a dry film by roll lamination.

[Step 3] Exposure Step

The CCL obtained in step 2 is placed in an exposure apparatus, and exposed according to patterns of the sensor electrodes 12, the lead wires 12c, and the external terminal electrodes 12d. If the area of a single pressure sensing element 100 is sufficiently smaller than the exposure area illuminable in a single shot, multiple pressure sensing elements 100 may be formed on a single substrate in a single shot, and then separated by dicing in a suitable step.

[Step 4] Development Step

The exposed CCL is loaded on a developing machine to form a pattern. The developing solution is typically a weak alkali solution. The dry film pattern remained on the CCL after the development serves as an etching resist in the etching step described later. After the etching resist is patterned by the development, the CCL and the etching resist are suitably rinsed with water so as to remove the developing solution adhered to the CCL and the etching resist.

[Step 5] Etching Step

The CCL, having formed thereon the etching resist composed of the patterned dry film, is then etched. The etching solution used here is typically a copper chloride containing solution, but is suitably selectable from chemical solutions capable of etching the Cu foil, without special limitation. By the etching, the sensor electrodes 12, the lead wires 12c, and the external terminal electrodes 12d are formed according to the predetermined patterns in the CCL. After completion of this step, the individual patterns are capped with the dry film remained thereon. The sensor electrode 12 includes the first electrode 12a and the second electrode 12b.

[Step 6] Step of Stripping Dry Film

After the etching step, the dry film remaining on the individual patterns is stripped. The stripping is typically proceeded by a technique of swelling and then lifting off the dry film using a weak-alkaline stripping solution. After the dry film is stripped off, the CCL is rinsed with water, and then subjected to rustproofing for protecting the exposed Cu pattern. In this way, the sensor electrodes 12, and the lead wires 12c are formed in the CCL.

[Step 7] Step of Coating Photo-Sensitive Coating Material

Next, on the CCL obtained in step 6, the insulating layer 13 is formed. More specifically, a predetermined thickness of the photo-sensitive coating material is formed by coating, so as to cover the support substrate 11, the sensor electrode 12, and the lead wires 12c on the CCL, and then dried to form the insulating layer 13. The coating may be implemented by bar coating, screen printing, or any other popular coating technique.

[Step 8] Step of Exposing Photo-Sensitive Coating Material

The thus formed insulating layer 13 is exposed to light selectively in the region excluding where the opening 13a is formed. By the exposure of light matched to the exposure sensitivity of the photo-sensitive coating material, only the portion exposed to light is photo-polymerized.

[Step 9] Step of Developing Photo-Sensitive Coating Material

The work is developed using a weak alkali solution in order to selectively remove the unexposed region in step 8 (that is, the region where the opening 13a is formed). As a consequence, the opening 13a is formed in the insulating layer 13, and thereby the sensor electrode 12 exposes inside the opening 13a. The height of the insulating layer 13, measured from the support substrate 11 at least at the top periphery of the opening 13a, is larger than the height of the sensor electrode 12 housed in the opening 13a. The development may be followed by additional baking at a predetermined temperature for a predetermined time, for the purpose of improving the strength of the insulating layer 13, depending on properties of the photo-sensitive coating material.

[Step 10] Surface Treatment Step

Partial regions of the sensor electrode 12, the lead wires 12c, and the external terminal electrodes 12d provided on the support substrate 11, which remain exposed without being covered with the insulating layer 13, are subjected to surface treatment by Ni/Au plating. Either electroplating or electroless plating is suitably selected for the plating.

[Step 11] Step of Forming Adhesion Layer

Next, the adhesion layer 30 is formed conforming to the geometry of the insulating layer 13. For example, the adhesion layer 30 may be formed by preparing an adhesive sheet having been punched out at a portion corresponded to the opening 13a, and by laminating the sheet onto the surface of the insulating layer 13, under proper alignment with the opening 13a. Alternatively, the adhesive may be coated on the insulating layer 13 by a printing means such as screen printing, under proper alignment with the insulating layer 13 having the opening 13a formed therein, to thereby form the adhesion layer 30. Still alternatively, an adhesive sheet having been punched out at a portion corresponded to the opening 13a may be laminated with the pressure sensing film 14 to form the adhesion layer 30, and the obtained stack may be bonded to the insulating layer 13 while placing the adhesion layer 30 in between as described later. In all cases, the adhesion layer 30 is not formed in the region corresponded to the opening 13a.

[Step 12] Step of Bonding Pressure Sensing Film

The pressure sensing film 14 is bonded to the surface of the insulating layer 13. Typically by using a vacuum press apparatus having been widely used for manufacture of flexible printed circuit board (FPC), and by press-bonding the insulating layer 13 and the pressure sensing film 14 under heating in vacuo, while placing the adhesion layer 30 in between, they may be successfully bonded while preventing air from being entrained between the layers. In this way, the pressure sensing film 14 is bonded to the insulating layer 13, excluding the region thereof corresponded to the opening 13a. Since, the height of the sensor electrode 12 is lower than the height of the top periphery of the opening 13a, when measured from the support substrate 11, so that the sensor electrode 12 and the pressure sensing film 14 are kept apart in the initial state where no external pressure is applied.

[Step 13] Step of Forming Reinforcing Plate for External Terminal Electrode

For the external terminal electrodes 12d of the pressure sensing element 100 intended to be plugged or unplugged to or from a connector, or to be used in a bonded form with an anisotropic conductive film (ACF), the steps below are optionally implemented. More specifically, in order to make the external terminal electrodes 12d appropriately rigid, a reinforcing plate (not illustrated) is formed on the external terminal electrodes 12d. The reinforcing plate is typically composed of a plate made of metal such as stainless steel or aluminum, or a film made of polyimide or polyethylene terephthalate, having a desired thickness, and is laminated with the external terminal electrodes 12d using a tacky agent or adhesive.

[Step 14] Step of Precision Punching of External Terminal Electrode

In many cases, the external terminal electrodes 12d of the pressure sensing element 100 is typically connected to external board or instrument through plugging or unplugging of a connector, or bonding with ACF. Accordingly, a high level of dimensional accuracy is often required for the punching which determines profile of the portion contributive to the connection. More specifically, the punching is implemented using a precisely-machined die, to satisfy a level of dimensional accuracy required for the external terminal electrodes 12d.

[Step 15] Step of Contour Punching of Pressure Sensing Element

Precision punching of the external terminal electrodes 12d is followed by a step of contour punching for determining an overall contour of the pressure sensing element 100.

The pressure sensing element 100 is manufactured by the steps 1 to 15 described above. The thus manufactured pressure sensing element 100 is then checked for dimensions of the individual portions, conduction performance of the sensor electrodes 12 and the lead wires 12c, and pressure-sensitive resistivity characteristic, and shipped as an accepted product if certain standards have been met. Alternatively, the pressure sensing element 100 obtained above may be electrically connected with the detection unit 210 to manufacture the pressure sensor 200. If the pressure sensing element 100 manufactured as described above has the sensor electrodes 12 and the lead wires 12c provided only on one surface thereof, the CCL with the support substrate may go through the individual processes of steps 1 to 15, in the form of roll.

<Second Embodiment>

Next, a pressure sensing element 300 and a pressure sensor 400 according to a second embodiment of this invention will be explained referring to FIG. 5 to FIG. 9. The pressure sensing element 300 of this embodiment is different from the pressure sensing element 100 of the first embodiment, in that it has a plurality of sensor electrodes 12. The pressure sensor 400 is different from the pressure sensor 200 in that it has a pressure sensing element 300 in place of the pressure sensing element 100.

Figure 5:
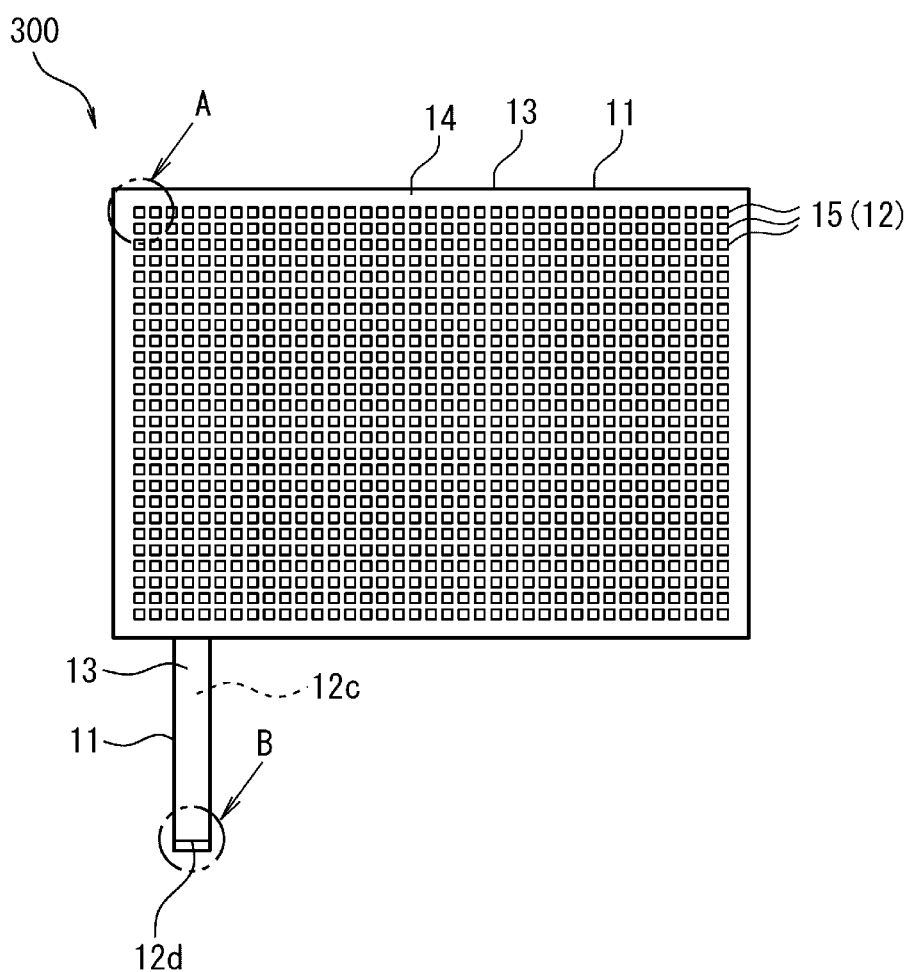
FIG. 5 A plan view illustrating a pressure sensing element according to a second embodiment of this invention.
Figure 6A:
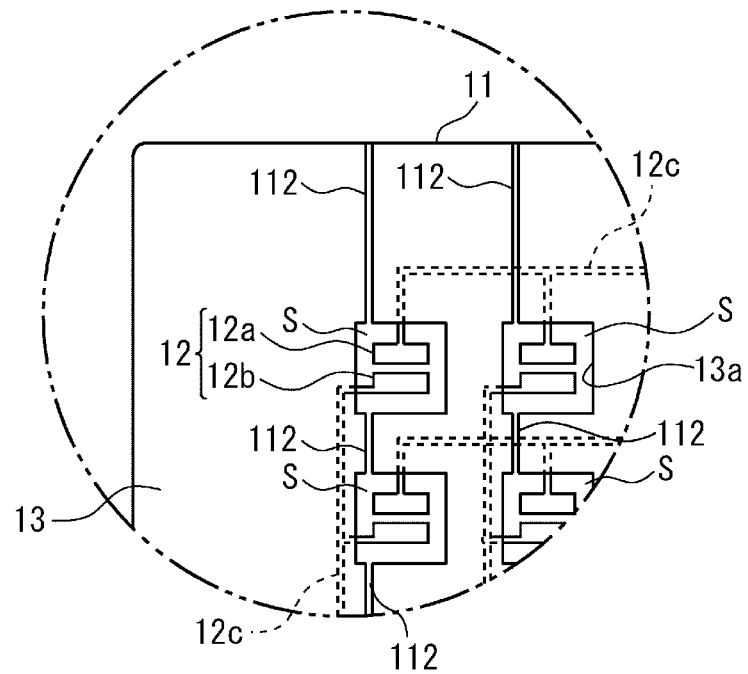
FIG. 6 (a) is a partial enlarged view of part "A" in FIG. 5, and (b) is a partial enlarged view of part "B" in FIG. 5.
Figure 6B:
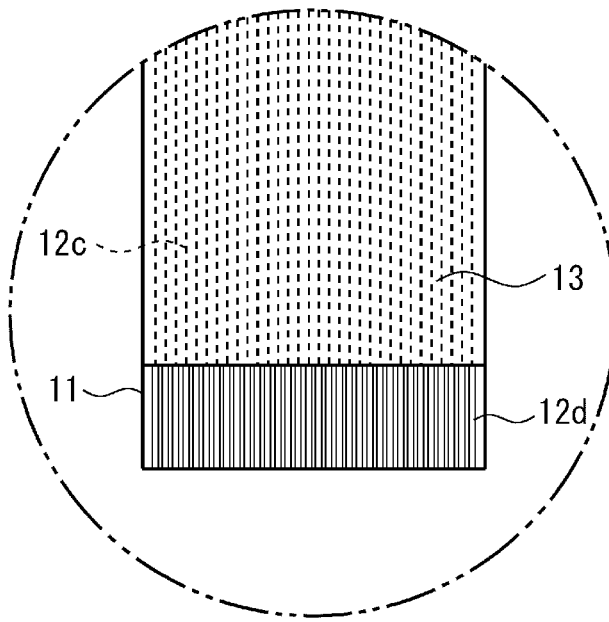
Figure 7A:
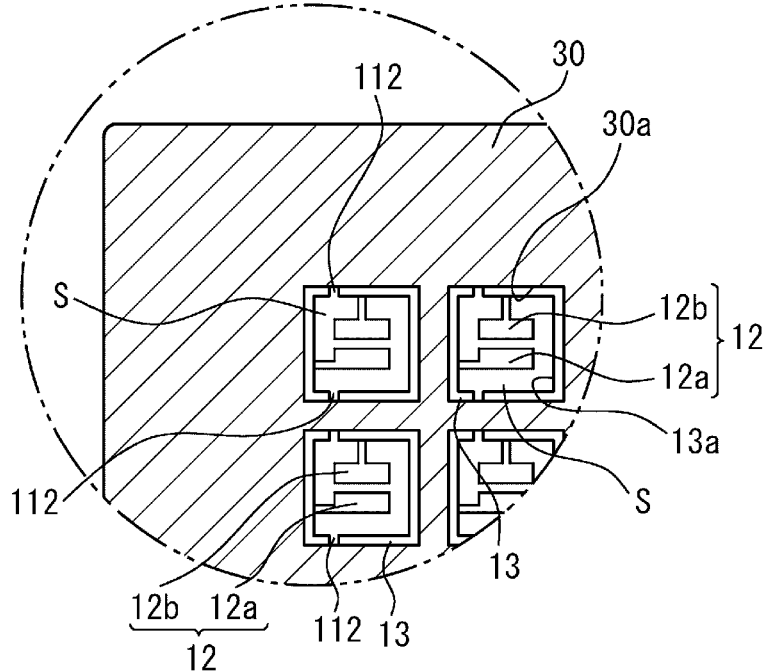
FIG. 7 (a) and (b) are partial enlarged views of part "A" in FIG. 5, with the pressure sensing film unillustrated.
Figure 8A:
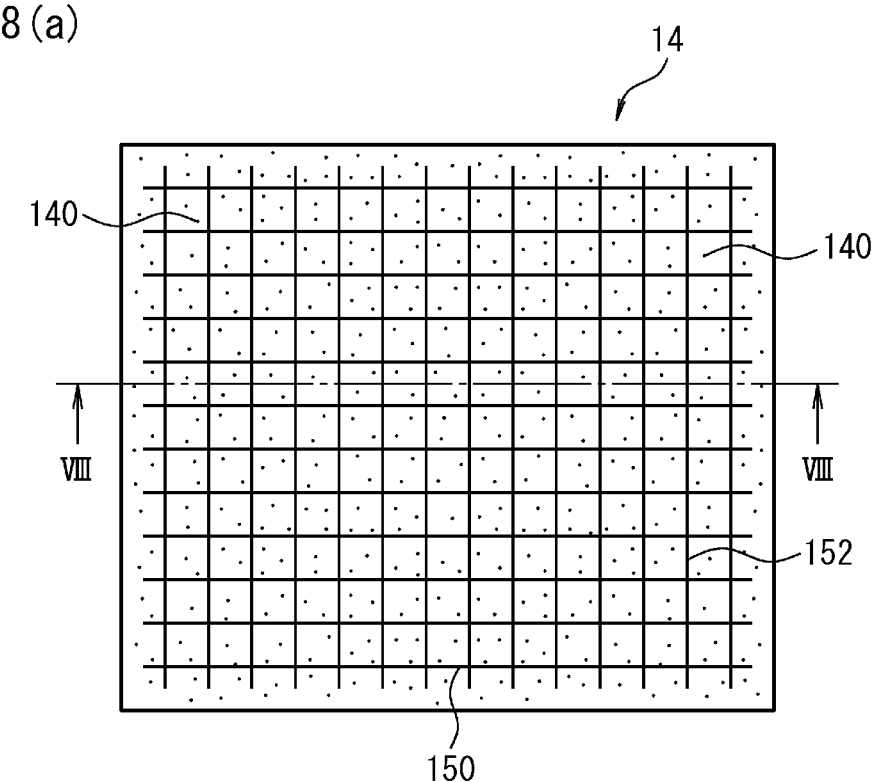
FIG. 8 (a) is a plan view of the pressure sensing film, viewed from the side faced to the sensor electrode, and (b) is across-sectional view taken along line VIII-VIII in (a).
Figure 8B:
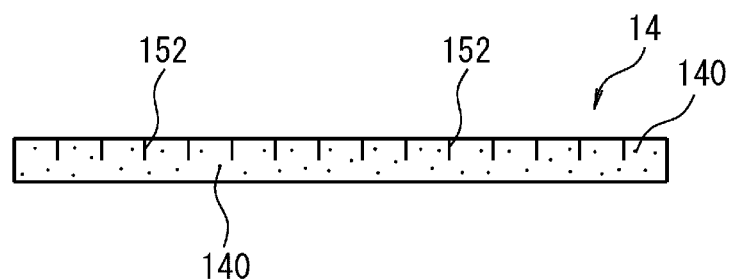
Figure 9:
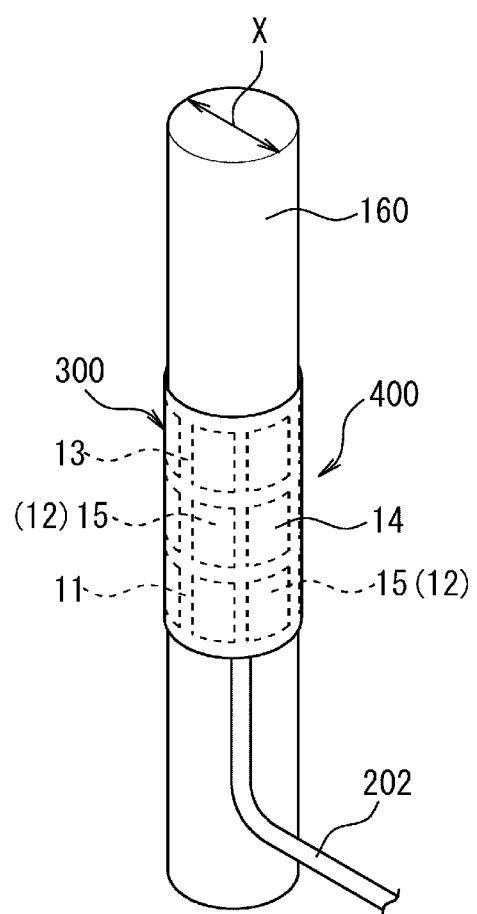
FIG. 9 A perspective view illustrating a pressure sensor having a pressure sensing element mounted on the surface of a cylinder having diameter X.

FIG. 5 is a plan view illustrating the pressure sensing element 300 according to the second embodiment of this invention. FIG. 6(a) is a partially enlarged view of part "A" in FIG. 5, and FIG. 6(b) is a partially enlarged view of part "B" in FIG. 5. FIGS. 7(a) and (b) are partially enlarged views of part "A" in FIG. 5, from which the pressure sensing film 14 has been removed, with the adhesion layer 30 hatched for easy viewing. FIG. 8(a) is a plan view of the pressure sensing film 14, viewed from the side faced to the sensor electrode 12, and FIG. 8(b) is a cross-sectional view taken along line VIII-VIII in FIG. 8(a). FIG. 9 is a perspective view illustrating a pressure sensor 400 having the pressure sensing element 300 mounted on the surface of a cylinder 160 having diameter X. The detection unit 210 is not illustrated in FIG. 9.

The pressure sensing element 300 is, as illustrated in FIG. 5, a multi-channel type element having a plurality of pressure sensor parts 15 provided on a single support substrate 11. Every single pressure sensor part 15 has the unillustrated sensor electrode 12 and the pressure sensing film 14 opposed thereto. The configuration of the pressure sensor part 15 may be referred to the pressure sensing element 100 of the first embodiment for convenience. In the pressure sensing element 300, the lead wires 12c drawn out from the individual sensor electrodes 12 are connected to the external terminal electrodes 12d. The pressure sensing element 300 is properly configured in the same way as the pressure sensing element 100, except that there are plurality of pressure sensor parts 15, and that the lead wires 12c and external terminal electrodes 12d are provided corresponding to the plurality of pressure sensor parts 15.

More specifically, as may be understood from the illustration of FIG. 5 and FIG. 6(a), in the pressure sensing element 300, there are provided the plurality of pressure sensor parts 15, in which the pressure sensing film 14 and the sensor electrodes 12 are opposed to each other. In the pressure sensing element 300, a single pressure sensing film 14 faces to the plurality of sensor electrodes 12. The pressure sensing film 14 is disposed over a wide area which covers the plurality of sensor electrodes 12. In other words, the plurality of sensor electrodes 12 share a single pressure sensing film 14. The pressure sensing film 14 in this embodiment covers, solely by itself, the plurality of sensor electrodes 12. Typically as shown in FIG. 5, a single pressure sensing film 14 covers all of the sensor electrodes 12.

By configuring the plurality of pressure sensor parts 15 by disposing a single pressure sensing film 14 so as to extend over the plurality of sensor electrodes 12, a process load for patterning or alignment of the pressure sensing film 14 may be relieved, and the configuration of the pressure sensing element 300 may be simplified. In addition, film materials are often manufactured according to the standard width, which is as wide as 500 mm, 1000 mm and so on. For this reason, when the array-type pressure sensing element 300 is manufactured, the productivity may dramatically be improved by disposing a single large pressure sensing film 14 so as to oppose with the plurality of sensor electrodes 12, as compared with the case where the pressure sensing films 14 are disposed according to an island pattern. In this specification, the "array-type" means a type having a sensor group which is configured by a plurality of sensor electrodes 12 arranged regularly.

The pressure sensing element 300 of this embodiment can provide an array-type pressure sensor 400 (see FIG. 9). In this embodiment, a plurality of pressure sensor parts 15 are formed by allowing a plurality of sensor electrodes 12 to oppose with a single pressure sensing film 14. Modified examples of this embodiment include a mode of embodiment in which a plurality of pressure sensor parts 15 are configured by allowing the individual sensor electrodes 12 to oppose with the respective pressure sensing films 14. In other words, the pressure sensing films 14 may be arranged in an island pattern corresponding to the individual sensor electrodes 12.

The pressure sensing element 300 has, as illustrated in FIG. 6(a), a plurality of sensor electrodes 12 each having the pair of first electrode 12a and the second electrode 12b. Each of the first electrode 12a and the second electrode 12b is respectively connected with the lead wire 12c, through which voltage is applied from an unillustrated voltage supply unit. The pressure sensing film 14, upon externally loaded with pressurizing force, is brought into contact with the sensor electrode 12 to bridge the first electrode 12a and second electrode 12b, thereby the first electrode 12a and the second electrode 12b are electrified, and current flows through the lead wire 12c.

The distance between every adjacent sensor electrode 12 may suitably be determined depending on applications of the pressure sensing element 300. The distance may be 1 mm or longer and 10 mm or shorter, for instance. Although FIG. 5 illustrates an exemplary mode wherein the plurality of sensor electrodes 12 form a highly-ordered matrix on the support substrate 11, this embodiment is not limited thereto. The plurality of sensor electrodes 12 may be arranged in a lattice pattern or in a staggered pattern, and even may be arranged randomly.

Figure 7B:
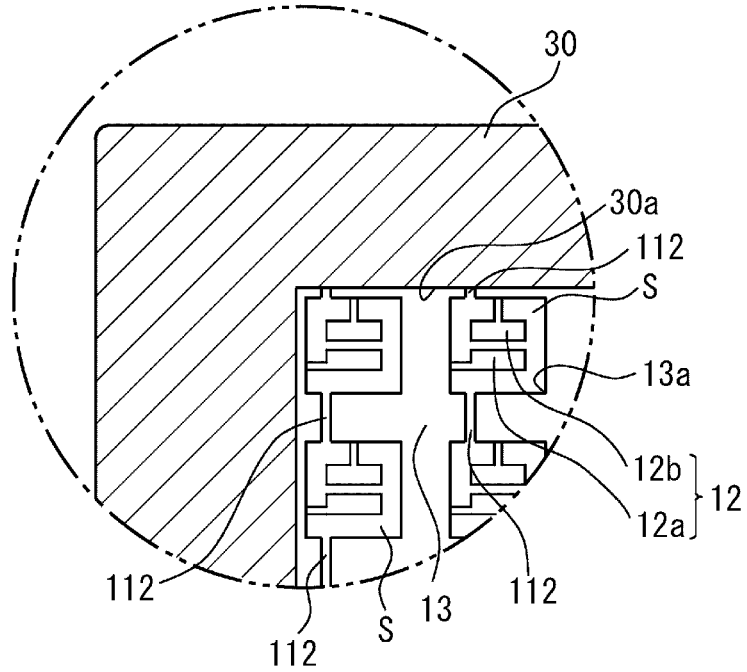

The pressure sensing element 300 has the adhesion layer 30 which binds the pressure sensing film 14 and the insulating layer 13 (see FIG. 7). The insulating layer 13 has first openings (openings 13a) through which the pressure sensing film 14 faces to the sensor electrodes 12 while placing the hollow space S in between. In this embodiment, the adhesion layer 30 has second openings (openings 30a). Each second opening contains the first opening (opening 13a) in a plan view. In other words, in this embodiment, the second openings (openings 30a) are larger than the first openings (openings 13a) in a plan view, and therefore contains the first openings (openings 13a). With such configuration, the adhesive which composes the adhesion layer 30 may be prevented from entering the hollow space S out from the second openings (openings 30a).

FIG. 7 (a) illustrates an exemplary mode wherein the first openings (openings 13a) and the second openings (openings 30a) surround each sensor electrode 12. FIG. 7 (b) illustrates a mode wherein a single second opening (opening 30a) surrounds a plurality of (all, for example) sensor electrodes 12. Inside the single second opening (opening 30a), each sensor electrode 12 is arranged inside each first opening (opening 13a).

As illustrated in FIG. 8 (a), in this embodiment, the single pressure sensing film 14 has, on the surface thereof which faces to the plurality of sensor electrodes 12, slits 150, 152 which extend from the outer surface up to the middle depth in the thickness-wise direction. The slits are formed so as to fall, in a plan view, between the plurality of sensor electrodes 12. In this embodiment, corresponding to the plurality of sensor electrodes 12 which are arranged to form a highly-ordered matrix, the slit 150 running in rows and the slit 152 running in lines are provided so as to cross each other. In a plan view, the slits 150, 152 are provided so that every single sensor electrode 12 falls in every square circumscribed by the slit 150 and the slit 152.

In this embodiment, as illustrated in FIG. 8 (b), the slit 150 extends from the outer surface on one side of the pressure sensing film 14 up to the middle depth in the thickness-wise direction and terminates there. For example, the slit 150 reaches approximately halfway of the thickness of the pressure sensing film 14, and terminates there. The slit 150 in this embodiment is an incision made into the outer surface in the thickness-wise direction, in which the opposing cut faces of each incision are substantially brought into contact to each other. Although not illustrated, the slit 150 may be a groove which recesses from the outer surface back into the thickness-wise direction. The groove is formed by carving using a V-cutter or dicing saw. The description regarding the slit 150 in this paragraph may suitably be applicable to the slit 152.

This embodiment makes it possible to configure the plurality of pressure sensor parts 15, by opposing the plurality of sensor electrodes 12 with a single pressure sensing film 14 as described above. In this mode of embodiment, it is anticipated that any two pressure sensor parts 15, if loaded with the pressurizing force at the same time, are electrically connected since they shares the pressure sensing film 14, and thereby a target signal may be contaminated with noise. In contrast, by providing the slits 150, 152 to the pressure sensing film 14, it now becomes possible to suitably prevent the noise. This is supposedly because, in a single pressure sensing film 14, the slits 150, 152 act as electric resistance against electrical conduction between one pressure sensor part 15 and the other pressure sensor part 15.

The pressure sensing element 300 described above is highly flexible like the pressure sensing element 100, and can show a good electrical reliability even in a bent state. The pressure sensor 400 provided with the pressure sensing element 300 may therefore be used while being placed on a curved surface of an object as illustrated in FIG. 9. For example, in the pressure sensor 400 of this embodiment, the pressure sensing element 300 is curved with a radius of curvature of 15 mm or smaller. Although depending on the overall design, the pressure sensing element 300 preferably has the predetermined distance "A", which is the spacing between the sensor electrode 12 and the pressure sensing film 14, of 5 μm or longer and 25 μm or shorter, and has a thickness of the pressure sensing film 14 of 6.5 μm or larger and 40 μm or smaller. With such configuration, the pressure sensing element 300 may be used while being bent up to a radius of curvature of 10 mm or smaller, and even up to a very small radius of curvature of 7 mm or smaller. While illustrated in FIG. 9 was an exemplary case where the pressure sensor 400 was used on the surface of a simple slim cylinder, the pressure sensor 400 may also be adaptable to a curved surface of an object with a more complex profile. For example, the pressure sensor 400 may be disposed over a part, or entire portion, of an area modeled on the human hand, to implement a hand-shaped, or glove-type pressure sensor. Also a pressure sensor 200, having the pressure sensing element 100 composed of a single sensor electrode 12, may be used while being placed on a surface with a complex texture, in the same way as the pressure sensor 400.

Alternatively, the pressure sensor 400, when disposed in the in-plane direction of an unillustrated mat of a bed, can sense how the body weight of a person lying on the bed is applied. The pressure sensor 400, when disposed behind a display unit of a tablet terminal, PC, electronic paper or the like, can detect the load applied by touching (typing) on the display unit, or two or more sites pressed at the same time.

Having described above the first embodiment and the second embodiment of this invention, this invention is not limited to the above-described embodiments, and may include various modifications and improved modes so long as the purpose of this invention will successfully be achieved.

For example, while all embodiments described above dealt with the exemplary case having the sensor electrodes 12 on one surface of the support substrate 11, this invention is not limited thereto. This invention encompasses the mode of embodiment having the sensor electrodes 12 and the pressure sensing film 14 provided on both surfaces of the support substrate 11. This invention is again not limited to the case where the film-type support substrate 11 is used as the substrate on which the sensor electrodes 12 are formed. This invention can embody the pressure sensing element 100 on various types of substrates capable of supporting the sensor electrode 12, and allowing thereon formation of the insulating layer 13 and pressure sensing film 14 in a stacked manner.

EXAMPLE

Examples of this invention, Comparative Example, and Reference Examples will be explained below.

A basic configuration of the individual Examples, Comparative Examples and Reference Examples was manufactured after the pressure sensor 200 of the first embodiment. More specifically, on a polyimide film (25 μm thick) as the support substrate 11, the sensor electrode 12 having a pair of first electrode 12a and second electrode 12b, the lead wires 12c and the external terminal electrodes 12d were formed. To thus obtained pressure sensing element 100, a detection unit 210 was connected, to obtain the pressure sensor 200. Both of the first electrode 12a and the second electrode 12b were designed to be 20 μm high and 1000 μm wide (linewidth), and spaced by 100 μm. The lead wires 12c were designed to be 13 μm high and 100 μm wide (linewidth). Next, the insulating layer 13 provided with the opening 13a was formed. Next, the adhesion layer 30 was formed over the surface of the insulating layer 13, and the pressure sensing film 14, which is a polyimide film containing carbon particles, was stacked thereon while placing the adhesion layer 30 in between, to thereby form the pressure sensor part 15, and to obtain the pressure sensing element 100. The pressure sensor part 15 was designed to be 4 mm$^2$ in area. The external terminal electrodes 12d and the detection unit 210 were electrically connected using the flexible wiring 202, to thereby manufacture the pressure sensor 200.

Regarding the pressure sensing elements 100 of the individual Examples, Comparative Example and Reference Examples, distance "A" from the sensor electrode 12 to the pressure sensing film 14, the thickness of the pressure sensing film 14, surface resistivity Rs and surface roughness Rz were varied as summarized in Table 1. Respectively in the individual Examples, Comparative Example and Reference Examples, the content of the carbon particles contained in the pressure sensing film 14 was controlled so as to adjust the surface resistivity Rs and the surface roughness Rz to the values summarized in Table 1.

According to the basic configuration described above and the specifications summarized in Table 1, the pressure sensors of the individual Examples, Comparative Example, and Reference Examples were manufactured, and evaluated for the pressure sensing characteristics as described below. Five samples were prepared respectively for the individual Examples, Comparative Example, and Reference Examples, and were evaluated. As for the evaluation of initial detection sensitivity and detection sensitivity under large load, described later, the minimum value and the maximum value of every five samples were listed in Table 1. As for the short-circuit test described later, evaluation of "not detected" was given when short-circuiting was detected in none of five samples, and "detected" was given even if only one sample showed short-circuiting. Results are summarized in Table 1.
[Evaluation of Initial Detection Sensitivity]

Each of the pressure sensors of the individual Examples, Comparative Example, and Reference Examples was placed on a flat surface, and the pressure sensor part 15 was gradually loaded from outside of the pressure sensing film 14, and the load under which electric conduction is initially detected was determined as initial detection sensitivity (N).
[Evaluation of Detection Sensitivity Under Large Load]

Each of the pressure sensors of the individual Examples, Comparative Example, and Reference Examples was placed on a flat surface, the pressure sensor part 15 having an area of 4 mm$^2$ was loaded with a load of 1.1 MPa (112.5 gf/mm$^2$), and the resistivity (Ω) was measured.
[Short-Circuit Test]

Each of the pressure sensors of the individual Examples, Comparative Example, and Reference Examples was wrapped around a 10 mm diameter glass rod, and occurrence of short-circuit was checked without externally loading the pressure sensor part 15 (i.e., in the initial state).

the distance "A" exceeding 25 μm was found to show an initial detection sensitivity of larger than 1000 N, showing a tendency higher than in other Examples.

Example 10 characterized by the pressure sensing film of thicker than 40 μm was found to show an initial detection sensitivity of larger than 1000 N, showing a tendency higher than in other Examples.

Example 13 characterized by the surface resistivity of the pressure sensing film exceeding 30000Ω was found to show a large difference between the maximum value and minimum value in the detection sensitivity under large load, showing a large variation among the values of five samples. This is supposedly due to a reduced amount of addition, and a poor dispersion as a consequence, of the carbon particles added to the pressure sensing film, as compared with other Examples. Reference Example 1 characterized by a surface resistivity of the pressure sensing film of smaller than 7000Ω was found to fail in forming the film durable for measurement, since the content of the carbon particles in the pressure sensing film was distinctively increased as compared with Examples, aiming at reducing the resistivity.

TABLE 1

| | Pressure sensing element | | | Evaluation of Pressure sensing characteristics | | | | |
|---|---|---|---|---|---|---|---|---|
| | | Pressure sensing film | | Initial detection sensitivity (N) | | Detection sensitivity under large load (Ω) | | Short-circuit test |
| | Distance A | Thickness | Surface resistivity | Surface roughness | | | | |
| | (μm) | (μm) | Rs (Ω/sq) | Rz (μm) | Min. | Max. | Min. | Max. | |
| Comparative Example 1 | 0 | 12.5 | 20000 | 0.1 | Short-circuited under 0 load | | 720 | 980 | Detected |
| Example 1 | 2.5 | 12.5 | 20000 | 0.1 | 88 | 110 | 750 | 1070 | Detected |
| Example 2 | 5 | 12.5 | 20000 | 0.1 | 220 | 250 | 980 | 1150 | Not detected |
| Example 3 | 10 | 12.5 | 20000 | 0.1 | 490 | 510 | 1300 | 1450 | Not detected |
| Example 4 | 15 | 12.5 | 20000 | 0.1 | 570 | 620 | 1420 | 1500 | Not detected |
| Example 5 | 25 | 12.5 | 20000 | 0.1 | 820 | 870 | 1490 | 1700 | Not detected |
| Example 6 | 40 | 12.5 | 20000 | 0.1 | 1200 | 1300 | 2100 | 2320 | Not detected |
| Example 7 | 15 | 6.5 | 20000 | 0.1 | 400 | 420 | 730 | 1050 | Not detected |
| Example 8 | 15 | 25 | 20000 | 0.1 | 740 | 790 | 1710 | 1940 | Not detected |
| Example 9 | 15 | 38 | 20000 | 0.1 | 870 | 920 | 2020 | 2280 | Not detected |
| Example 10 | 15 | 50 | 20000 | 0.1 | 1100 | 1300 | 2200 | 2340 | Not detected |
| Example 11 | 15 | 12.5 | 7000 | 0.1 | 570 | 590 | 1010 | 1060 | Not detected |
| Example 12 | 15 | 12.5 | 30000 | 0.1 | 560 | 640 | 1740 | 1910 | Not detected |
| Reference Example 1 | 15 | 12.5 | 1000 | 0.1 | — | | — | | — |
| Example 13 | 15 | 12.5 | 50000 | 0.1 | 670 | 830 | 2130 | 2880 | Not detected |
| Example 14 | 15 | 12.5 | 20000 | 0.3 | 640 | 690 | 1530 | 1750 | Not detected |
| Example 15 | 15 | 12.5 | 20000 | 0.45 | 630 | 690 | 1720 | 1870 | Not detected |
| Reference Example 2 | 15 | 12.5 | 20000 | 0.75 | — | | — | | — |
| Example 16 | 5 | 6.5 | 7000 | 0.1 | 69 | 110 | 680 | 950 | Not detected |
| Example 17 | 25 | 38 | 30000 | 0.45 | 880 | 950 | 2180 | 2380 | Not detected |

As summarized in Table 1, the initial detection sensitivity and the detection sensitivity under large load were actually measured for all Examples, proving that the configurations are suitable for practical use.

The results of evaluation of the individual Examples revealed the tendencies below. Examples 16 and 17, having all of the distance "A" between the pressure sensing film and the sensor electrode, the thickness of the pressure sensing film, the surface resistivity, and the surface roughness designed according to the preferable ranges, were found to be particularly good in the initial detection sensitivity and the dynamic range.

Example 1 characterized by the distance "A" shorter than 5 μm was occasionally found to cause short-circuiting when bent under a severe condition. Example 6 characterized by Reference Example 2, designed to have a distinctively large surface roughness of the pressure sensing film, was again found to fail in forming the film durable for measurement.

Meanwhile, Comparative Example, characterized by a distance "A" of zero between the pressure sensing film and the sensor electrode, was found to cause short-circuiting even in the flat state.

The above-described embodiments also encompass the technical ideas described below.

(1) A pressure sensing element which includes:

an electro-conductive pressure sensing film;

a sensor electrode provided at a position faced to the pressure sensing film; and an insulating layer which creates a predetermined distance between the pressure sensing film and the sensor electrode so as to keep them apart from each other, the pressure sensing film being a resin film containing carbon particles.

(2) The pressure sensing element according to (1), wherein the predetermined distance, measured in the initial state while keeping the pressure sensing film nearly flat, is 5 μm or longer and 25 μm or shorter.

(3) The pressure sensing element according to (1) or (2), wherein the pressure sensing film has a thickness of 6.5 μm or larger and 40 μm or smaller.

(4) The pressure sensing element according to any one of (1) to (3), wherein the Young's modulus of the pressure sensing film is 5 GPa or smaller.

(5) The pressure sensing element according to any one of (1) to (4), wherein the pressure sensing film has a surface resistivity of 7 kΩ/sq or larger and 30 kΩ/sq or smaller.

(6) The pressure sensing element according to any one of (1) to (5), wherein the surface of the pressure sensing film, faced to the sensor electrode, has a surface roughness Rz of 0.10 μm or larger and 0.50 μm or smaller.

(7) The pressure sensing element according to any one of (1) to (6), wherein the pressure sensing film has a heat resistance of 260° C. or higher.

(8) The pressure sensing element according to any one of (1) to (7), wherein the resin composing the pressure sensing film contains polyimide or polyamide-imide as a main ingredient.

(9) The pressure sensing element according to (8), wherein the Young's modulus of the pressure sensing film is smaller than the Young's modulus of a film of the same thickness composed of the resin which composes the pressure sensing film.

(10) The pressure sensing element according to any one of (1) to (9), which includes a plurality of pressure sensor parts each configured by the pressure sensing film and the sensor electrode opposed to each other, and a single sheet of pressure sensing film being opposed to the plurality of the sensor electrodes.

(11) The pressure sensing element according to (10), wherein the single sheet of pressure sensing film has, on the side thereof faced to the sensor electrodes, a slit which extends from the outer surface up to the middle depth in the thickness-wise direction, and the slit falls, in a plan view, between the plurality of sensor electrodes.

(12) The pressure sensing element according to any one of s 1 to 11, further including a flexible substrate, the sensor electrode is formed at least on one surface of the substrate, and the pressure sensing element being configure to be flexible.

(13) The pressure sensing element according to any one of (1) to (12), further including an adhesion layer which bonds the pressure sensing film and the insulating layer, the insulating layer has a first opening through which the pressure sensing film and the sensor electrode are opposed while placing a hollow space in between, and the adhesion layer has a second opening which contains the first opening in a plan view.

(14) A pressure sensor which includes:

the pressure sensing element described in any one of (1) to (13); and a detection unit which is electrically connected with the pressure sensing element so as to detect contact resistance between the pressure sensing film and the sensor electrode.

(15) The pressure sensor according to (14), wherein the pressure sensing element curves with a radius of curvature of 15 mm or smaller.

The invention claimed is:

1. A pressure sensing element comprising:
an electro-conductive pressure sensing film comprising a resin and carbon particles, the resin comprising polyimide or polyamide-imide as a main ingredient;
a sensor electrode provided at a position faced to the pressure sensing film; and
an insulating layer which creates a predetermined distance between the pressure sensing film and the sensor electrode so as to keep them apart from each other,
wherein a surface of the pressure sensing film, faced to the sensor electrode, has a surface roughness Rz of 0.10 μm or larger and 0.50 μm or smaller.

2. The pressure sensing element according to claim 1, wherein the predetermined distance, measured in the initial state while keeping the pressure sensing film nearly flat, is 5 μm or longer and 25 μm or shorter.

3. The pressure sensing element according to claim 1, wherein the pressure sensing film has a thickness of 6.5 μm or larger and 40 μm or smaller.

4. The pressure sensing element according to claim 1, wherein the Young's modulus of the pressure sensing film is 5 GPa or smaller.

5. The pressure sensing element according to claim 1, wherein the pressure sensing film has a surface resistivity of 7 kΩ/sq or larger and 30 kΩ/sq or smaller.

6. The pressure sensing element according to claim 1, wherein the pressure sensing film has a heat resistance of 260 ° C. or higher.

7. The pressure sensing element according to claim 1, wherein the Young's modulus of the pressure sensing film is smaller than the Young's modulus of a film of the same thickness composed of the resin which composes the pressure sensing film.

8. The pressure sensing element according to claim 1, comprising a plurality of pressure sensor parts each configured by the pressure sensing film and the sensor electrode opposed to each other, and a single sheet of pressure sensing film being opposed to the plurality of the sensor electrodes.

9. The pressure sensing element according to claim 8, wherein the single sheet of pressure sensing film has, on the side thereof faced to the sensor electrodes, a slit which extends from the outer surface to a middle depth in the thickness-wise direction, and the slit falls, in a plan view, between the plurality of sensor electrodes.

10. The pressure sensing element according to claim 1, further comprising a flexible substrate, the sensor electrode is formed at least on one surface of the substrate, and the pressure sensing element being configured to be flexible.

11. The pressure sensing element according to claim 1, further comprising an adhesion layer provided between a lower surface of the pressure sensing film and an upper surface of the insulating layer for bonding the pressure sensing film with the insulating layer, the insulating layer has a first opening through which the pressure sensing film and the sensor electrode are opposed while placing a hollow space in between, and the adhesion layer has a second opening larger than the first opening, the second opening entirely surrounding the first opening in a plan view.

12. A pressure sensor comprising:

the pressure sensing element described in claim 1; and a detection unit which is electrically connected with the pressure sensing element so as to detect contact resistance between the pressure sensing film and the sensor electrode.

13. The pressure sensor according to claim 12, wherein the pressure sensing element curves with a radius of curvature of 15 mm or smaller.

14. The pressure sensing element according to claim 1, wherein when force is not applied to the pressure sensing element, the pressure sensing film does not directly contact the sensor electrode, wherein when force is applied to the pressure sensing element, the pressure sensing film directly contacts the sensor electrode.

* * * * *